(12) United States Patent
Kim

(10) Patent No.: US 9,554,768 B2
(45) Date of Patent: Jan. 31, 2017

(54) MOBILE X-RAY IMAGING APPARATUS AND METHOD OF CONTROLLING THE SAME

(71) Applicant: SAMSUNG ELECTRONICS CO., LTD., Suwon-si (KR)

(72) Inventor: Myeong Je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 166 days.

(21) Appl. No.: 14/506,833

(22) Filed: Oct. 6, 2014

(65) Prior Publication Data

US 2015/0117614 A1 Apr. 30, 2015

(30) Foreign Application Priority Data

Oct. 25, 2013 (KR) ........................ 10-2013-0127596

(51) Int. Cl.
*H05G 1/24* (2006.01)
*A61B 6/00* (2006.01)
*H02J 7/00* (2006.01)
*H05G 1/32* (2006.01)

(52) U.S. Cl.
CPC .............. *A61B 6/56* (2013.01); *A61B 6/4405* (2013.01); *A61B 6/54* (2013.01); *H02J 7/0031* (2013.01); *H02J 7/0068* (2013.01); *H05G 1/32* (2013.01)

(58) Field of Classification Search
CPC ........... A61B 6/56; A61B 6/4405; A61B 6/54; H05G 1/32; H02J 7/0031; H02J 7/0068
USPC ........................................ 378/101–103, 198
See application file for complete search history.

(56) References Cited

U.S. PATENT DOCUMENTS 4,797,907 A * 1/1989 Anderton ................. H05G 1/10
378/101
2002/0149345 A1 10/2002 Takano et al.

FOREIGN PATENT DOCUMENTS

JP 2009-153847 A 7/2009

OTHER PUBLICATIONS

Communication dated Mar. 23, 2015 issued by the European Patent Office in counterpart European Patent Application No. 14187784.5.

* cited by examiner

*Primary Examiner* — Courtney Thomas
(74) *Attorney, Agent, or Firm* — Sughrue Mion, PLLC

(57) ABSTRACT

A mobile X-ray imaging apparatus and a method of controlling the mobile X-ray imaging apparatus are provided. The mobile X-ray imaging apparatus includes an X-ray source mounted in a movable main body, a battery configured to supply operating power to the X-ray source, a charger configured to supply charging power to charge the battery, and a controller configured to block charging of the battery while X-rays are radiated.

17 Claims, 26 Drawing Sheets

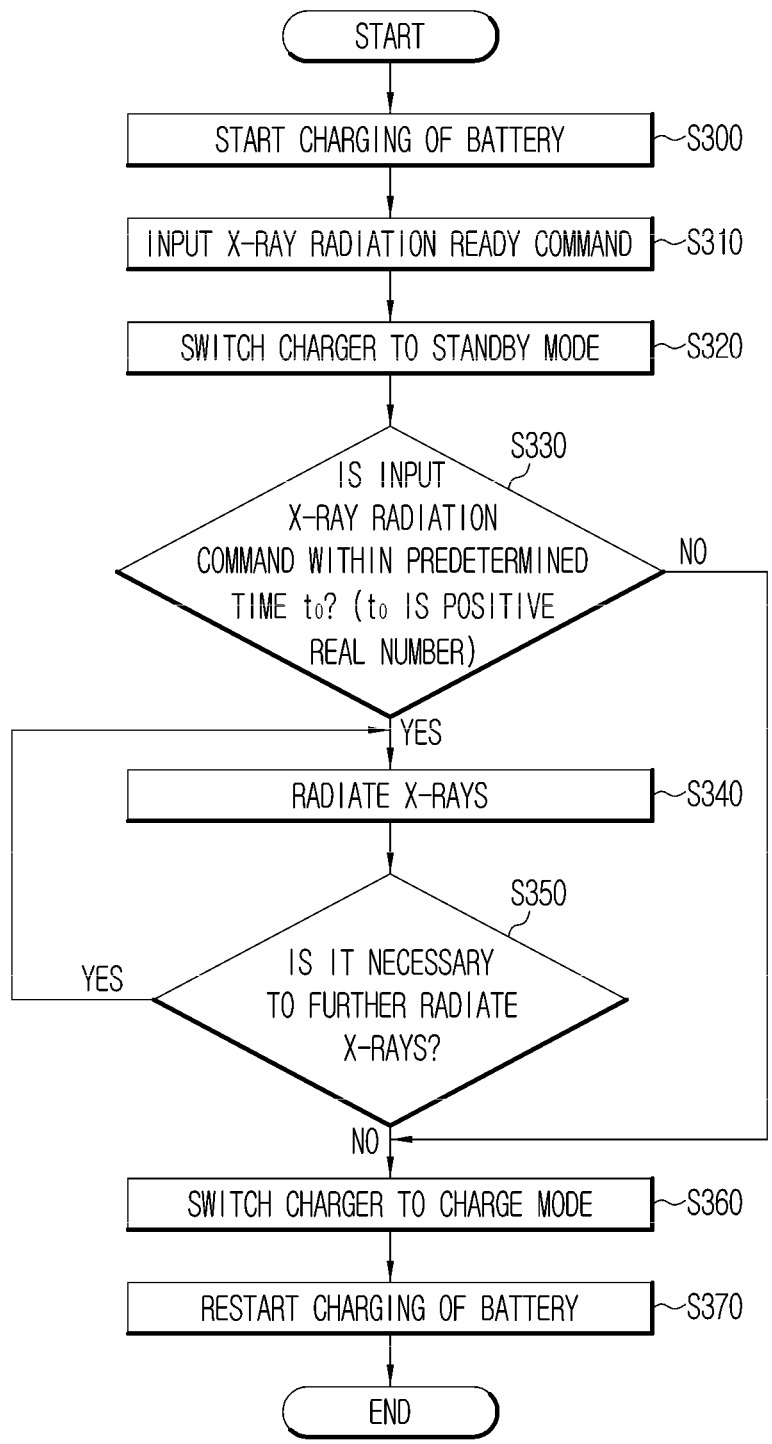

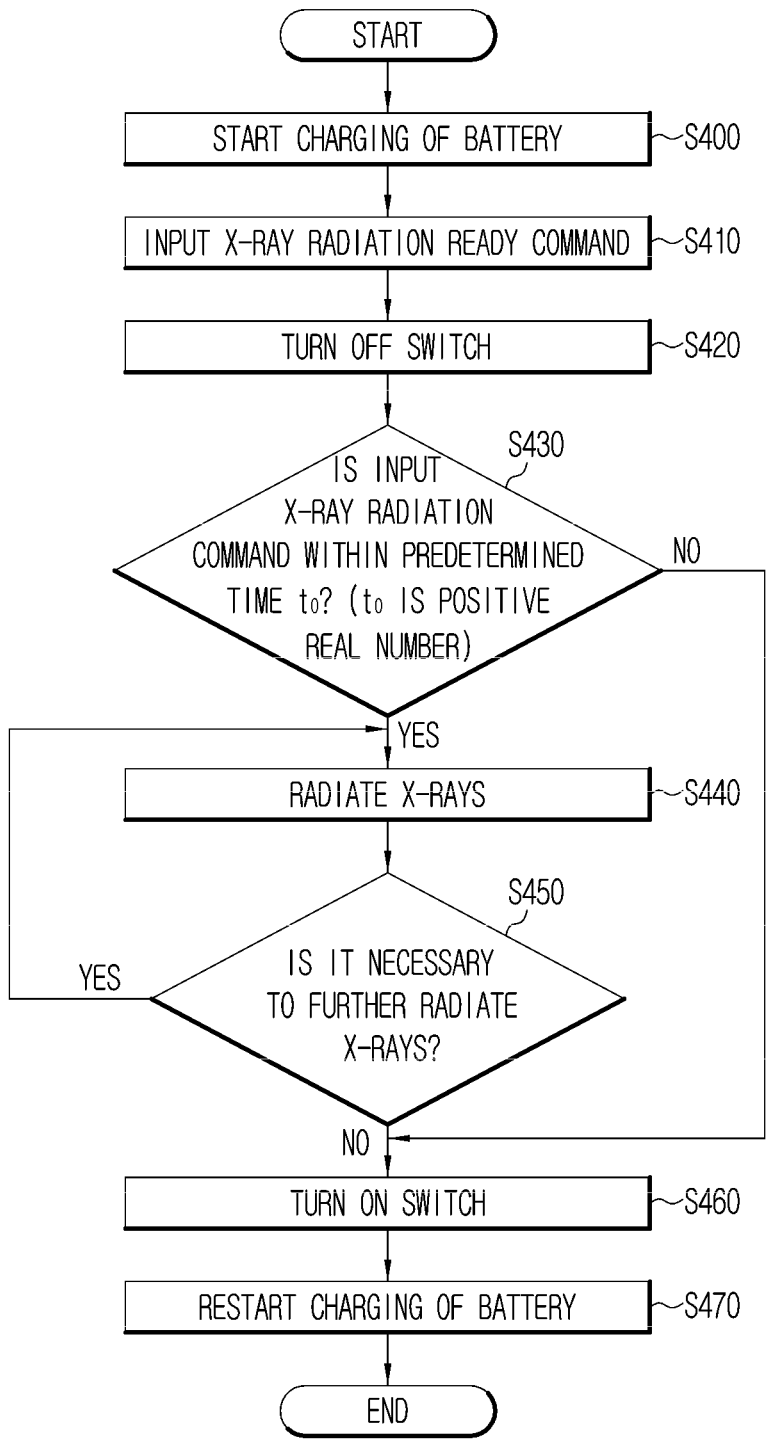

MOBILE X-RAY IMAGING APPARATUS AND METHOD OF CONTROLLING THE SAME

CROSS-REFERENCE TO RELATED APPLICATION

This application claims priority from Korean Patent Application No. 2013-0127596, filed on Oct. 25, 2013 in the Korean Intellectual Property Office, the disclosure of which is incorporated herein by reference in its entirety.

BACKGROUND

1. Field

Apparatuses and methods consistent with the exemplary embodiments relate to a mobile X-ray imaging apparatus for generating X-ray images by transmitting X-rays through an object and a method of controlling the same.

2. Description of the Related Art

An X-ray imaging apparatus is a non-invasive diagnostic apparatus that can image an internal structure of an object by radiating X-rays onto the object and detecting X-rays transmitted through the object. An object can include, for example, a body part of a patient, an animal or luggage.

In a general X-ray imaging apparatus, since an X-ray source and an X-ray detector are fixed in a predetermined location, a patient needs to move to a laboratory in which the X-ray imaging apparatus is provided. Further, the patient needs to move his or her body to accommodate the apparatus in order to perform X-ray imaging.

However, since it is difficult for patients who have difficulty moving to be imaged using the general X-ray imaging apparatus, a mobile X-ray imaging apparatus capable of performing X-ray imaging at any location has been developed.

Since the X-ray source is mounted in a movable main body and a portable X-ray detector is used in the mobile X-ray imaging apparatus, it is possible to perform X-ray imaging on patients who have difficulty moving by bringing the X-ray imaging apparatus directly to the patients.

SUMMARY

An exemplary embodiment provides a mobile X-ray imaging apparatus and a method of controlling the same which can prevent charging power generated from a charger from entering an X-ray source when X-ray imaging is performed.

According to an aspect of an exemplary embodiment, there are provided a mobile X-ray imaging apparatus and a method of controlling the same, which may include an X-ray source mounted in a movable main body, a battery configured to supply operating power to the X-ray source, a charger configured to supply charging power to charge the battery, and a controller configured to block charging of the battery while X-rays are radiated.

A supply path of the operating power and a supply path of the charging power may form at least one node The apparatus may further include a switch provided in the supply path of the charging power.

The controller may turn off the switch and block charging of the battery.

The controller may switch the charger to a standby mode and block charging of the battery.

The charger may not generate the charging power in the standby mode.

The apparatus may further include an inputter configured to receive an X-ray radiation ready command and an X-ray radiation command and the controller may block charging of the battery when the X-ray radiation ready command is input.

The controller may perform control such that the charging of the battery is restarted when the radiation command is not input within a predetermined time after the ready command is input.

According to another aspect of an exemplary embodiment, there is provided a method of controlling a mobile X-ray imaging apparatus which includes a movable main body, a battery configured to supply operating power to the main body, and a charger configured to supply charging power to charge the battery. The method includes determining whether X-rays are radiated when the charging power is supplied to the battery and blocking supply of the charging power to the battery when it is determined that the X-rays are radiated.

In the mobile X-ray imaging apparatus, a supply path of the operating power and a supply path of the charging power may form at least one node.

The mobile X-ray imaging apparatus may further include a switch provided in the supply path of the charging power.

The blocking of the charging power to the battery may include turning off the switch.

The blocking of the supply of the charging power to the battery may include switching the charger to a standby mode.

The charger may not generate the charging power in the standby mode.

The determining of whether an X-ray source radiates X-rays may be performed by verifying whether an X-ray radiation ready command is input through an inputter.

The method may further include restarting charging of the battery when an X-ray radiation command is not input within a predetermined time after the ready command is input.

According to the mobile X-ray imaging apparatus and the method of controlling the same, it is possible to prevent the charging power generated from the charger from entering the X-ray source when X-ray imaging is performed, and thus it is possible to prevent overload of the charger.

BRIEF DESCRIPTION OF THE DRAWINGS

These and/or other aspects of an exemplary embodiment will become apparent and more readily appreciated from the following description of the exemplary embodiments, taken in conjunction with the accompanying drawings of which:

FIG. 10 is a flowchart illustrating a method of controlling a mobile X-ray imaging apparatus according to an exemplary embodiment; and FIG. 11 is a flowchart illustrating a method of controlling a mobile X-ray imaging apparatus according to another exemplary embodiment.

DETAILED DESCRIPTION

Hereinafter, a mobile X-ray imaging apparatus and a method of controlling the same will be described in detail with reference to the accompanying drawings according to the following exemplary embodiments.

Figure 1A:
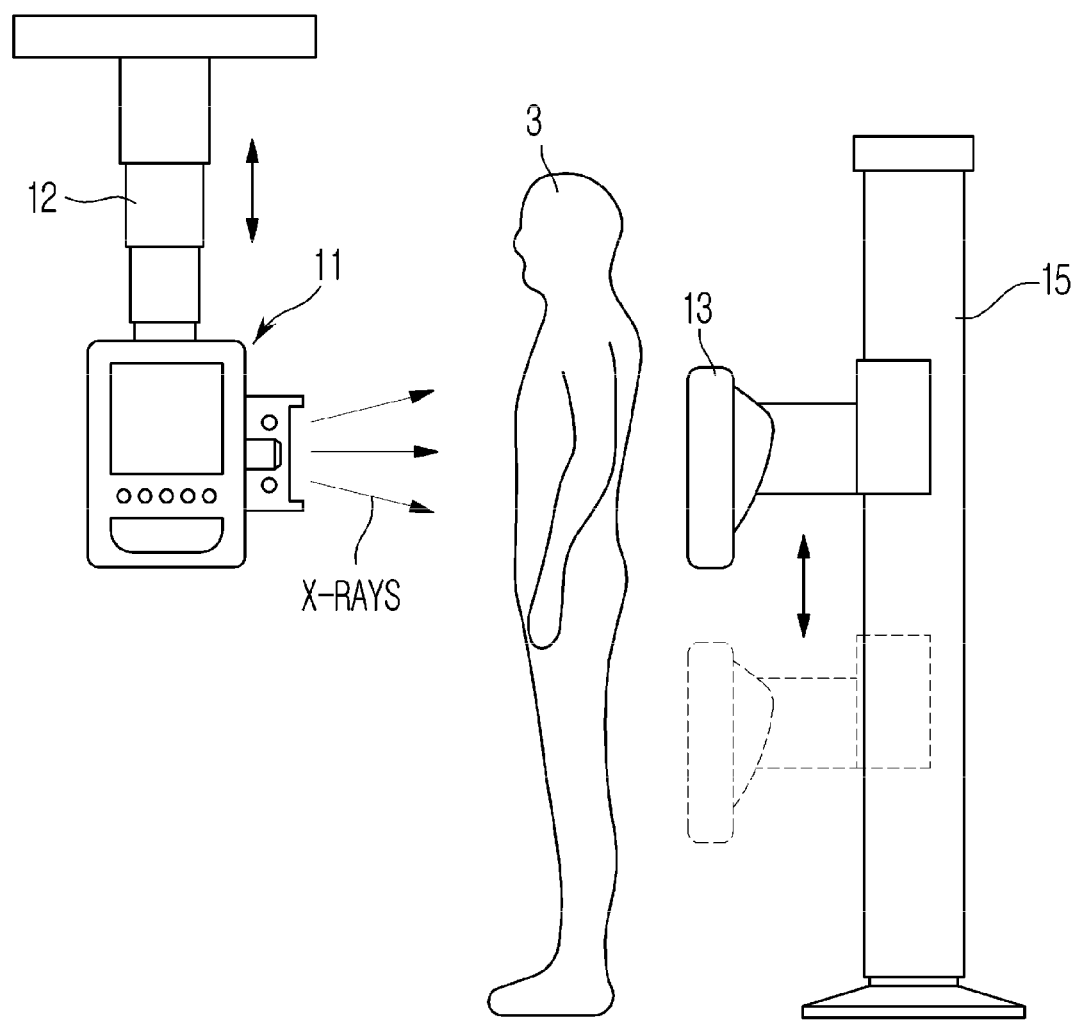
FIG. 1A is a diagram illustrating an appearance of a general X-ray imaging apparatus according to an exemplary embodiment and FIG. 1B is a diagram illustrating an appearance of a mobile X-ray imaging apparatus according to an exemplary embodiment.
Figure 1B:
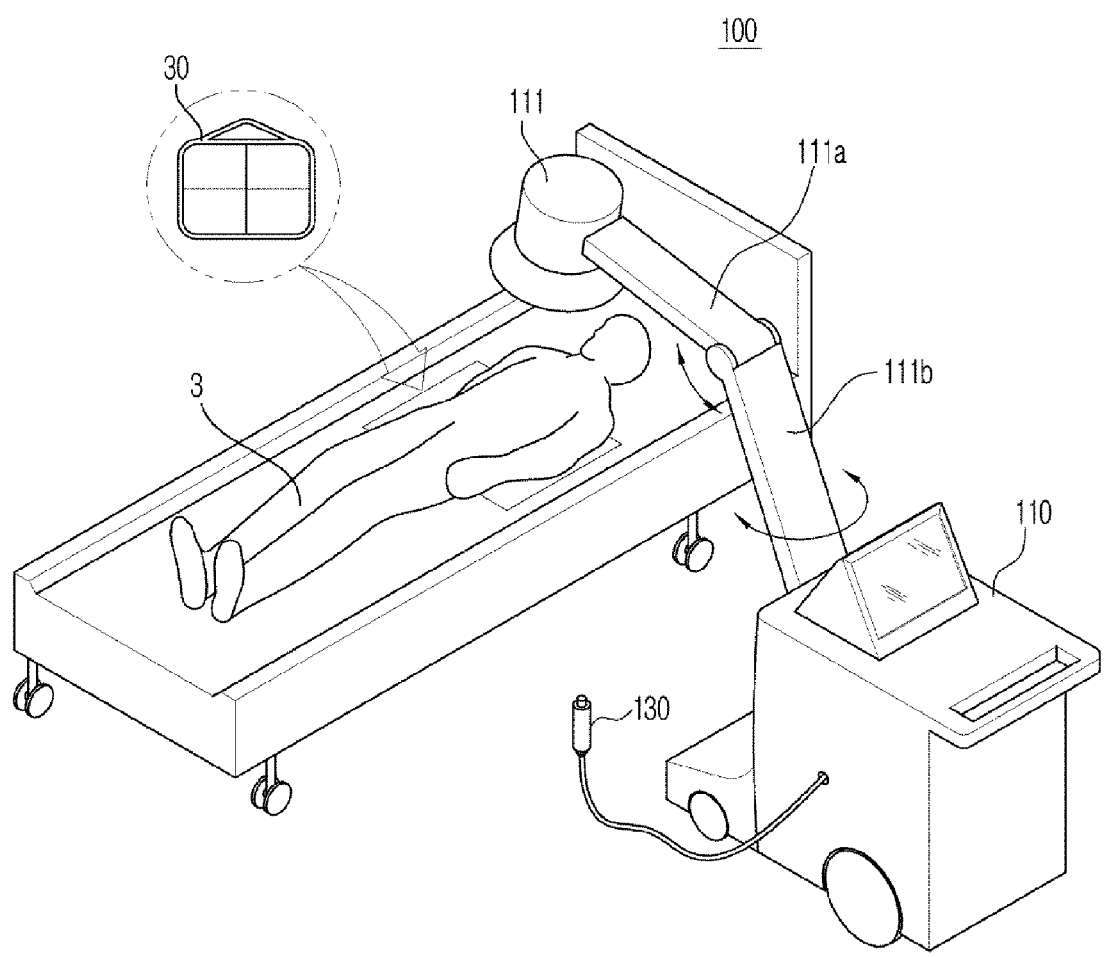

FIG. 1A is a diagram illustrating an appearance of a general X-ray imaging apparatus according to an exemplary embodiment and FIG. 1B is a diagram illustrating an appearance of a mobile X-ray imaging apparatus according to an exemplary embodiment.

In the general X-ray imaging apparatus, an X-ray source 11 and an X-ray detector 13 are fixed in a predetermined location. For example, as illustrated in FIG. 1A, the X-ray source 11 is connected to an arm 12 mounted in, for example, a ceiling of a laboratory, and the X-ray detector 13 is connected to a housing 15 fixed to, for example, a floor of the laboratory. The arm 12, which is connected to the X-ray source 11, is extendable. The X-ray source 11 is movable in a vertical direction with respect to the ground, and the X-ray detector 13 is also movable in a vertical direction along with the housing 15. That is, in the general X-ray imaging apparatus 10, the X-ray source 11 and the X-ray detector 13 move only in a predetermined direction within a predetermined space.

However, as illustrated in FIG. 1B, in a mobile X-ray imaging apparatus 100, the X-ray source 111 and the X-ray detector 30 are freely movable in an arbitrary three-dimensional (3D) space. The X-ray detector 30 is portable. Specifically, the X-ray source 111 may be mounted in a movable main body 110 through a support arm 111A. The support arm 111A may be vertically rotatably mounted in a support frame 111B, and the support frame 111B may be horizontally rotatably mounted in a side of the main body 110. As a result, the support arm 111A is rotatable. Specifically, an inclination of the support arm 111A may be changed, and thus the X-ray source 111 may be freely moved. In addition, the mobile X-ray imaging apparatus 100 uses the portable X-ray detector 30 and the X-ray detector 30 may also be provided in an arbitrary 3D space.

Figure 2:
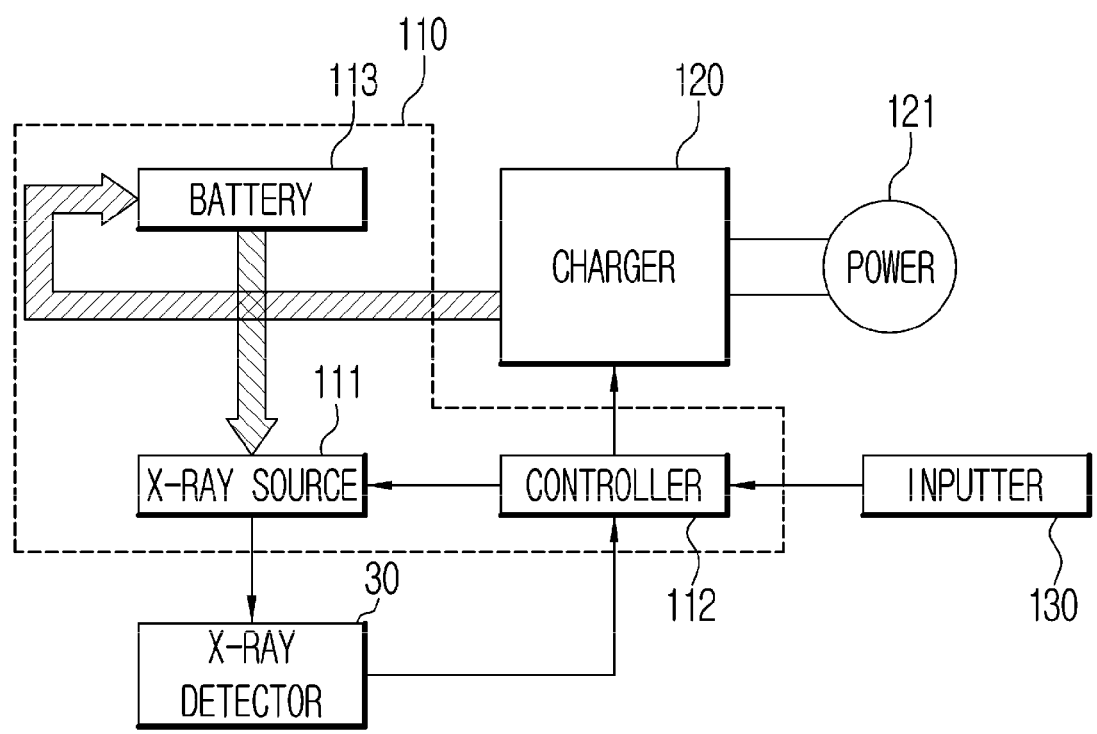
FIG. 2 is a control block diagram illustrating a mobile X-ray imaging apparatus according to an exemplary embodiment.

FIG. 2 is a control block diagram illustrating a mobile X-ray imaging apparatus according to an exemplary embodiment. In FIG. 2, a thin arrow indicates a flow of control and a thick arrow indicates a power supply path.

As illustrated in FIG. 2, the mobile X-ray imaging apparatus 100 according to the exemplary embodiment may include a main body 110 having an X-ray source 111, a controller 112, and a battery 113, an X-ray detector 30, a charger 120, and an inputter 130.

In order to obtain an X-ray image of an object, the X-ray source 111 may generate X-rays and radiate the generated X-rays onto the object. Here, the object may include a living body of a human or an animal, or a part of the human or animal, but the object is not limited thereto. The object may include any object of which an internal structure can be imaged by the mobile X-ray imaging apparatus 100.

The X-ray source 111 is supplied with power and generates X-rays. X-ray energy may be controlled by tube voltage, and a strength or a dose of X-rays may be controlled by tube current and an X-ray exposure time.

The X-ray detector 30 may detect X-rays that are radiated from the X-ray source 111 and transmitted through the object, and convert the detected X-rays into an electrical signal.

As described above, the X-ray detector 30 may transmit and receive mutually generated signals with the main body via wireless communication or wired communication through a physically connected cable.

The X-ray detector may include film based cassettes, computed radiography (CR) based cassettes, digital radiography (DR) based cassettes, or the like, but the exemplary embodiments are not limited thereto.

The controller 112 may be accommodated inside the main body 110. The controller 112 may control the X-ray source 111 in order to control X-ray generation, receive the electrical signal from the X-ray detector 30, and generate X-ray images. In addition, in order to prevent charging power from entering the X-ray source 111, charging of the battery 113 may be controlled. This will be further described below.

The battery 113 may supply operating power to the main body 110, specifically, to the X-ray source 111. In this case, the operating power may refer to power generated from the battery 113.

Unlike the general X-ray imaging apparatus, the mobile X-ray imaging apparatus 100 of the exemplary embodiment may be moved to a desired place and perform X-ray imaging. Therefore, in order to stably receive power necessary for operating the apparatus, the mobile X-ray imaging apparatus 100 includes the battery 113.

The battery 113 may include a lithium polymer battery but the exemplary embodiment is not limited thereto.

The battery 113 may be provided inside the main body 110 or may be detachably provided outside of the main body 110. Hereinafter, in the exemplary embodiments, the battery 113 is provided inside the main body 110.

The charger 120 may supply charging power to charge the battery 113. In this case, the charging power may refer to power generated from the charger 120.

The charger 120 is connected to a power supplier 121 and may be supplied with power from the power supplier 121. This supplied power is controlled by a user's input or operations in the apparatus and the charging power may be supplied to the battery 113.

Here, the user uses the mobile X-ray imaging apparatus 100 to diagnose an object 3. The user may be a medical staff person, such as a doctor, a radiologist, or a nurse, but the user is not limited thereto. Any user who uses the mobile X-ray imaging apparatus 100 may be included.

The charger 120 may be switched to a charge mode or a standby mode depending on the user's input or operations performed in the apparatus. In the charge mode, the charger 120 may supply the charging power to the main body 110 such that the battery 113 is charged. In the standby mode, the charger 120 may not supply the charging power to the main body 110. For example, when the battery 113 is discharged, the user may set the charger 120 as the charge mode and charge the battery 113. As a result, when the battery 113 is completely charged, the user may switch the charger 120 to the standby mode such that the charging power is no longer supplied.

As illustrated in FIG. 2, in the mobile X-ray imaging apparatus 100 including the battery 113 and the charger 120, problems may occur when X-ray imaging is performed while the battery 113 is being charged. Hereinafter, problems with respect to an existing mobile X-ray imaging apparatus will be described with reference to FIGS. 3A to 3C.

Figure 3A:
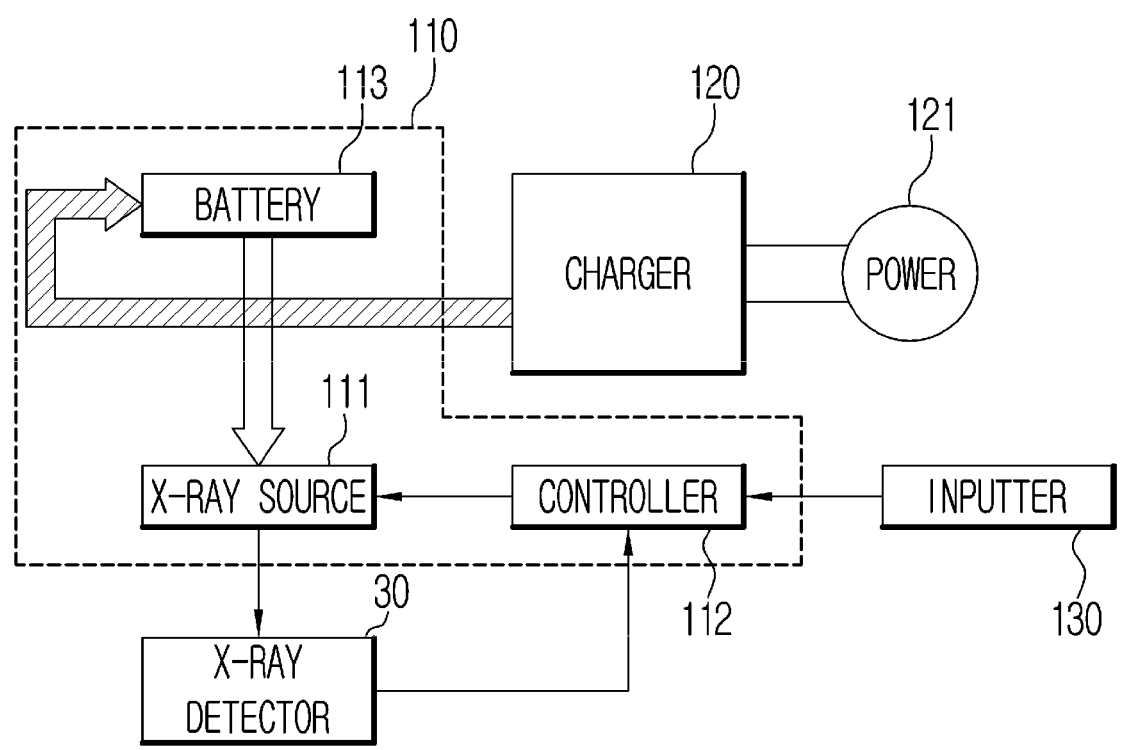
FIGS. 3A to 3C are diagrams illustrating problems of an existing mobile X-ray imaging apparatus.
Figure 3B:
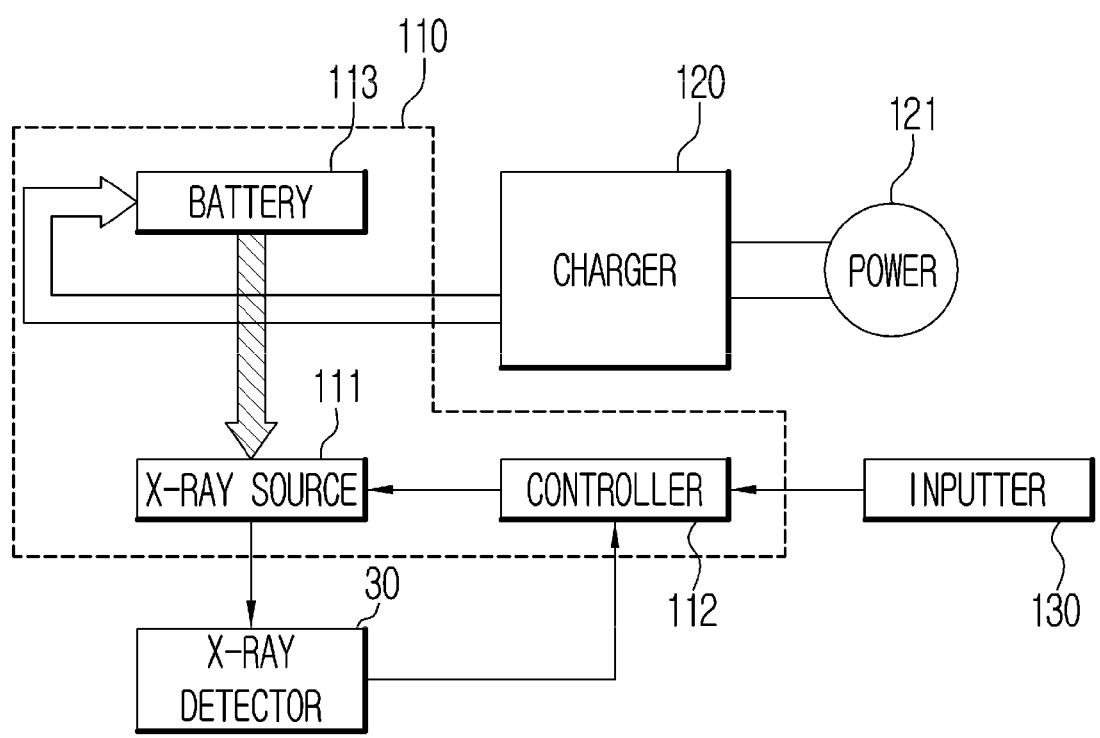

FIG. 3B is a control block diagram illustrating an existing mobile X-ray imaging apparatus in which X-rays are radiated while a battery is not being charged. A shaded section indicates a power supply path.

In general, a capacity of the battery 113 used in the mobile X-ray imaging apparatus 100 is 288 V7Ah and this capacity may be used for one hour when 288 V-7A is constantly used. The general X-ray source 111 has 32 kW of power consumption.

When a voltage of 288 V is supplied from the battery 113 having a capacity of 288 V7Ah to the X-ray source 111, having power consumption of 32 kW, maximum current of 111 A flows in the X-ray source 111.

Hereinafter, as illustrated in FIG. 3B, a path through which the operating power supplied from the battery 113 flows to the X-ray source 111 is referred to as an operating power supplying path.

FIG. 3A is a control block diagram illustrating an existing mobile X-ray imaging apparatus in which a battery is being charged when X-rays are not radiated. A shaded section indicates a power supply path.

In general, in order to charge the battery 113 having a capacity of 288 V7Ah, the charger 120 which outputs 288 VDC may constantly output current of 1.7 A.

As described above, the charger 120 may set the charge mode or the standby mode. In the charge mode, a voltage of 288 VDC and a current of 1.7 A are constantly provided. In the standby mode, the charging power is not provided.

Hereinafter, as illustrated in FIG. 3A, a path through which the operating power, supplied from the charger 120, flows to the battery 113 is referred to as a charging power supplying path.

Figure 3C:
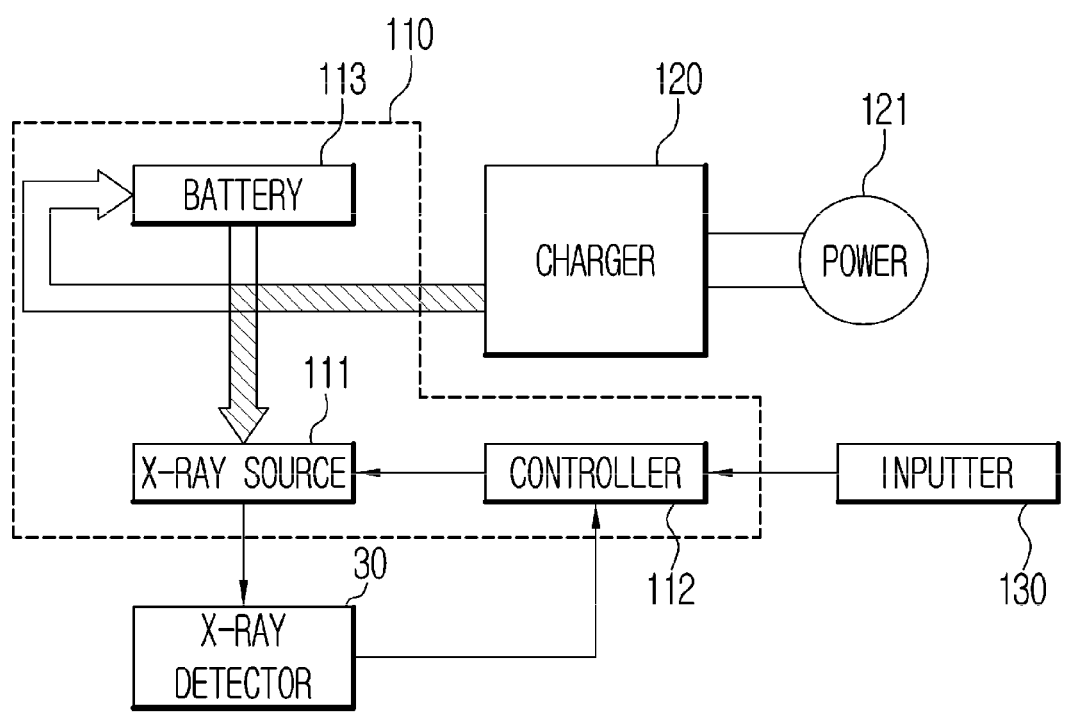

FIG. 3C is a control block diagram illustrating an existing mobile X-ray imaging apparatus in which X-rays are radiated while a battery is being charged. A shaded section indicates a power supply path.

As illustrated in FIGS. 3A and 3B, the operating power and the charging power are supplied through separate supplying paths. However, in the existing mobile X-ray imaging apparatus, an operating power supplying path and a charging power supplying path are provided in the same node. That is, as illustrated in FIG. 3C, the operating power supply path and the charging power supply path may form at least one node.

Under these conditions, problems may occur when charging and X-ray imaging are simultaneously performed. Specifically, since the operating power supplying path and the charging power supplying path form at least one node, the operating power may flow along the charging power supplying path and the charging power may flow along the operating power supplying path. In this case, when the X-ray source 111 radiates X-rays, it is required to supply the operating power and the voltage of the charger 120 may be higher than the voltage of the battery 113. Accordingly, the charging power may enter the X-ray source 111. That is, while the charging power generated from the charger 120 flows along the charging power supplying path, a flowing direction thereof may be changed to the operating power supplying path in the node and the charging power may enter the X-ray source 111.

As described above, whereas charging current output from the charger 120 is 1.7 A while the battery 113 is being charged, maximum operating current that is required when the X-ray source 111 radiates X-rays is 111 A. That is, maximum operating current flowing through the X-ray source 111 is about 65 times that of the charging current.

Therefore, in order to radiate X-rays, the charger 120 needs to generate a charging current that is about 65 times higher than usual. As a result, the charger 120 is overloaded. Therefore, when X-rays are radiated while the battery is being charged, the charging power is prevented from entering the X-ray source 111 and thus the X-ray source 111 needs to be supplied with the operating power from the battery 113.

Referring again to FIG. 2, in the mobile X-ray imaging apparatus according to the exemplary embodiment, the controller 112 may control modes of the charger 120. As described above, the charger 120 includes the charge mode and the standby mode. When these modes are used, it is possible to prevent the charging power from entering the X-ray source 111.

Specifically, the controller 112 may switch the mode of the charger 120 by classifying whether X-rays are radiated or not. For example, in order to charge the battery 113 before X-rays are radiated, the controller 112 may set the charger 120 to the charge mode. In order to radiate X-rays before charging is completed, the controller 112 may set the charger 120 to the standby mode first. When X-ray radiation ended, the controller 112 may perform control such that the charger 120 is switched to the charge mode again and the battery 113 is recharged.

The inputter 130 may receive a command from the user and deliver the command to the controller 112. The command input by the inputter 130 may include an X-ray radiation ready command or an X-ray radiation command. For example, a user may input the X-ray radiation ready command through the inputter 130 for imaging of the X-ray imaging apparatus. Then, when preparation for imaging is complete, the user may input the X-ray radiation command so that the X-ray source 111 radiates X-rays.

The inputter 130 may include at least one of a switch, a keyboard, a trackball, or a touch screen, and may also be provided in the form of a foot switch or a foot pedal.

In addition, the inputter 130 may also include a hand switch by which the user can input a command by holding or gripping the inputter with his or her hand and pressing the switch with his or her thumb or finger.

The inputter 130 is not limited to the above-described exemplary embodiments. However, for convenience of description, it is assumed and described below that the inputter 130 includes the hand switch. In addition, it is assumed and described that the user may input the ready command and the radiation command through the hand switch.

Figure 4A:
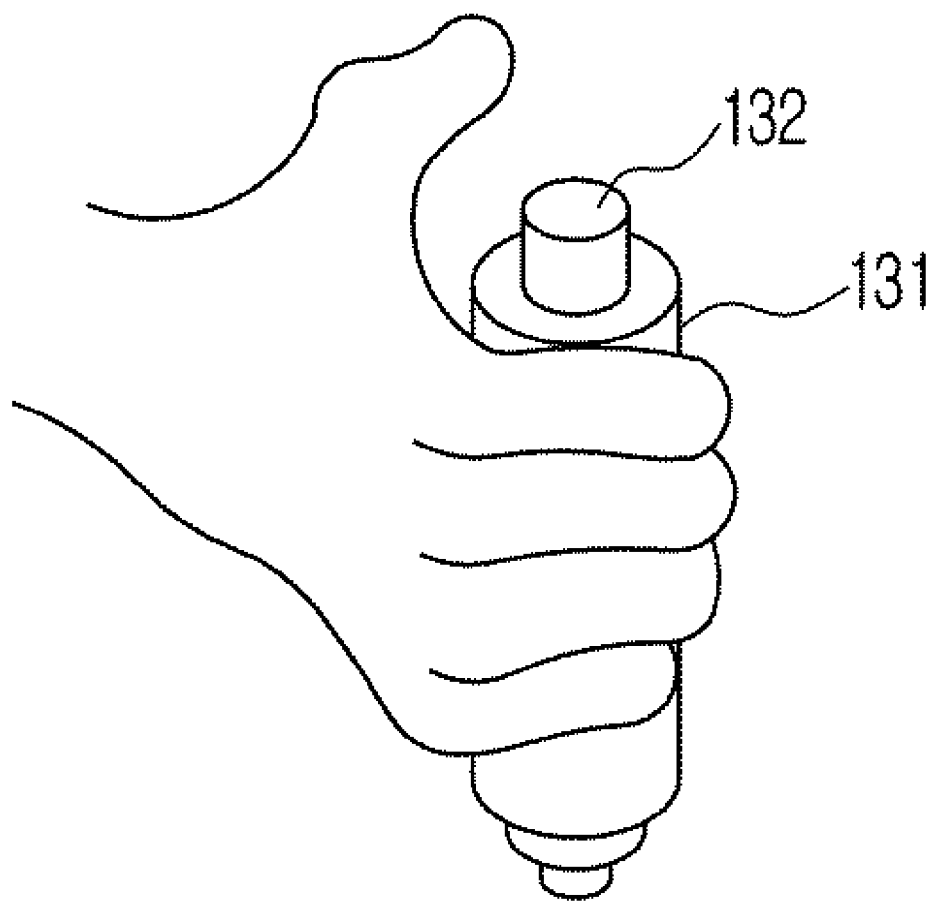
FIGS. 4A to 4C are diagrams illustrating a method of inputting a command by a user through an inputter.
Figure 4B:
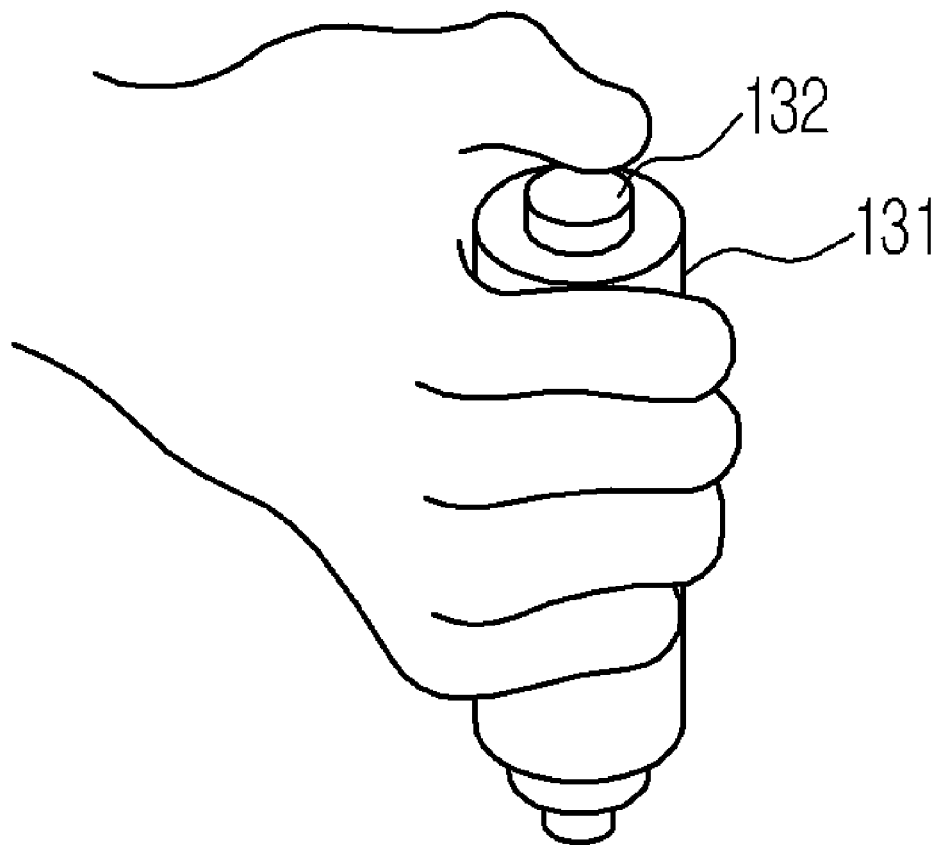
Figure 4C:
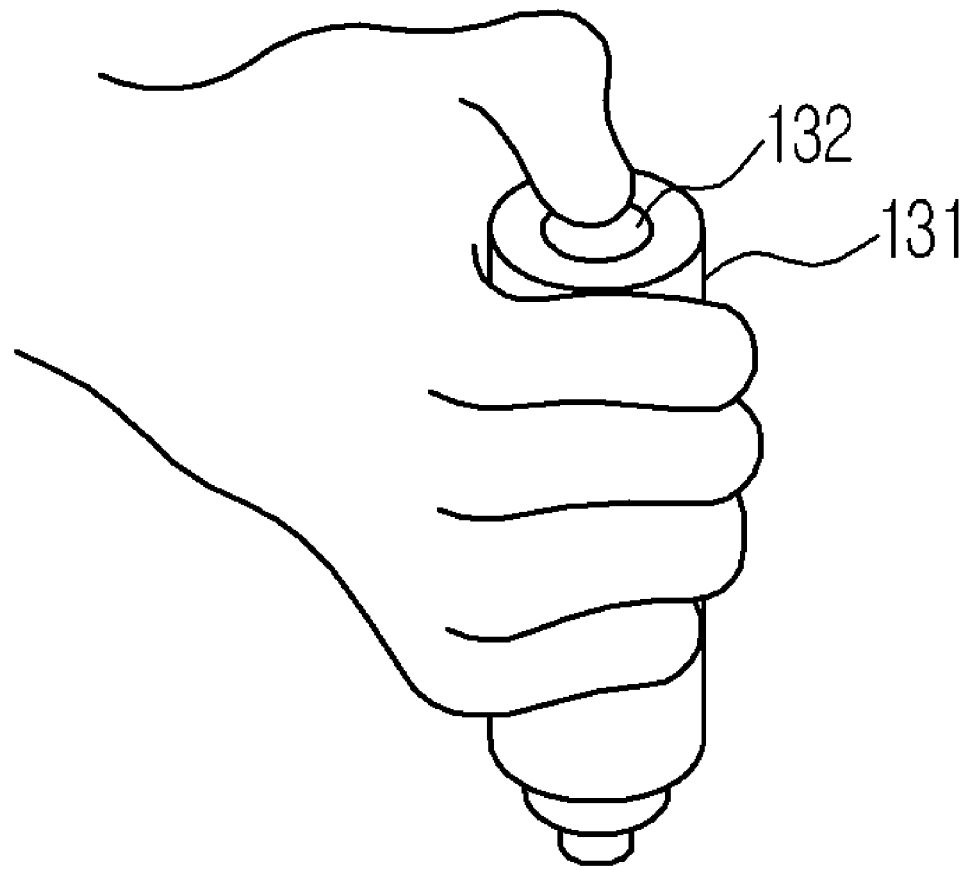

FIGS. 4A to 4C are diagrams illustrating a method of inputting a command by the user through the inputter.

As illustrated in FIGS. 4A to 4C, the inputter 130 may include a gripping part 131 and a button 132. The inputter 130 may be implemented as the hand switch, and thus may include the cylindrical gripping part 131 and the button 132 projecting from an upper surface thereof.

As illustrated in FIG. 4A, the user may grip or hold on to the inputter 130 through the gripping part 131. For example, it is possible to grip the gripping part 131 with four fingers other than a thumb. In this manner, by gripping the inputter 130, the user may press the button 132 projecting from the upper surface of the inputter 130 and input a control command.

As illustrated in FIG. 4B, the user may input a predetermined first command by applying pressure of a first threshold pressure or higher and less than a second threshold pressure to the button 132. In this case, the predetermined first command may be the X-ray radiation ready command. The first threshold pressure and the second threshold pressure can be determined by the user, however, this is merely an exemplary embodiment in the first threshold pressure and the second threshold pressure can be determined in other ways.

In addition, as illustrated in FIG. 4C, the user may input a predetermined second command by applying pressure of the second threshold pressure or higher to the button 132. In this case, the predetermined second command may be the X-ray radiation command.

As illustrated in FIGS. 4B and 4C, the first threshold pressure may be lower than the second threshold pressure. As a result, inputting of the first command may be necessary to input the second command. This is because, in order to apply pressure of the second threshold pressure or higher, it is first necessary to apply pressure of the first threshold pressure or higher and less than the second threshold pressure.

When the first command is the X-ray radiation ready command and the second command is the X-ray radiation command, the X-ray radiation command may be input after the X-ray radiation ready command is input. That is, X-ray radiation may be performed after the X-ray radiation ready command is input.

The inputter 130 may receive a command for switching the mode of the charger 120 in addition to the X-ray radiation ready command or the X-ray radiation command. Specifically, the first command may include the X-ray radiation command and a command for switching the charger 120 to the standby mode.

FIGS. 5A to 5D illustrate a series of control processes of the user controlling the mobile X-ray imaging apparatus through the inputter according to an exemplary embodiment. The left sides of FIGS. 5A to 5D illustrate a method of the user inputting a command through the inputter 130 according to the exemplary embodiment, and right sides thereof illustrate a method of controlling a power supply by the user's input according to the exemplary embodiment. The shaded section in the right sides of FIGS. 5A to 5D indicates a power supply path. Hereinafter, it is assumed and described that FIGS. 5A to 5D are sequentially arranged according to an occurrence in time.

Figure 5A:
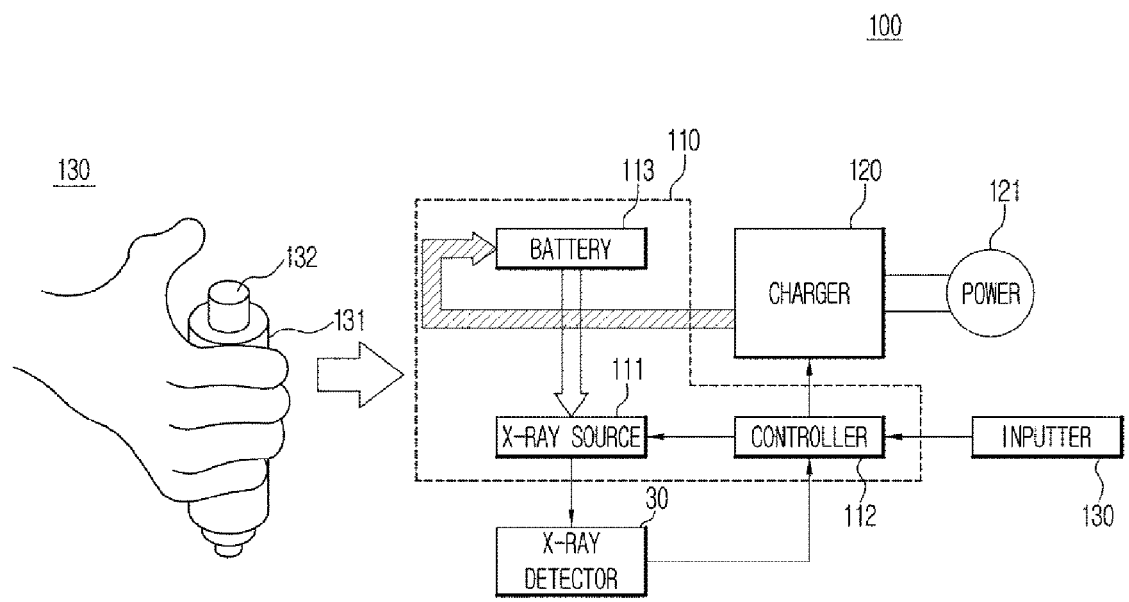
FIGS. 5A to 5D illustrate a series of control processes made by a user controlling a mobile X-ray imaging apparatus through an inputter according to an exemplary embodiment.

FIG. 5A exemplifies a case in which the battery 113 is being charged when no command is input to the mobile X-ray imaging apparatus. Since the battery 113 is being charged, the charger 120 may be set to the charge mode.

Referring to the left side of FIG. 5A, the user does not press the button 132 of the inputter 130. Not pressing may include applying pressure of less than the first threshold pressure.

Since there is no input and the battery 113 is being charged, the charger 120 is in the charge mode. As illustrated on the right side of FIG. 5A, the charging power may be supplied from the charger 120 to the battery 113. In this case, a path of supplying the charging power is the charging power supplying path.

Figure 5B:
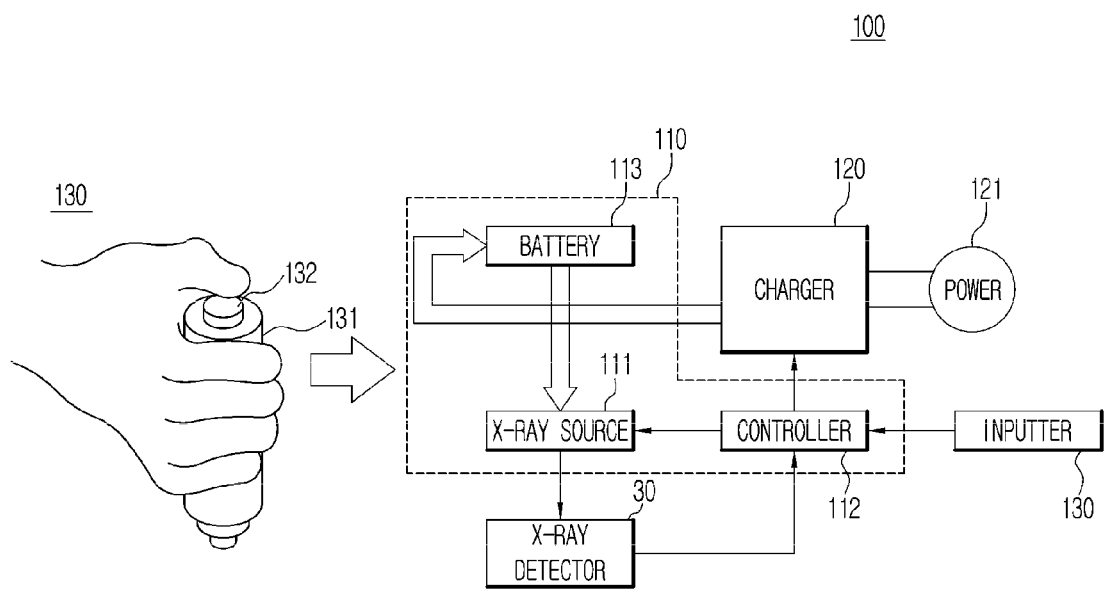

FIG. 5B exemplifies a case in which the X-ray radiation ready command is input to the mobile X-ray imaging apparatus while the battery is being charged.

When X-ray imaging is performed without control of the charging current, the charging current may enter the X-ray source 111 as illustrated in FIG. 3B. In this case, overcurrent flows and thus the charger 120 may be overloaded. Therefore, it is necessary to control the charging current according to a predetermined input of the user before X-rays are radiated.

As illustrated, as shown on the left side of FIG. 5B, the user may input the first command through the inputter 130. The first command may be the X-ray radiation ready command. The X-ray radiation ready command may be a command for controlling the mobile X-ray imaging apparatus 100 to have an optimal condition for radiating X-rays before the X-rays are radiated.

When the user inputs the X-ray radiation ready command, the controller 112 may switch the charger 120 to the standby mode in response to the command. This is because the charger 120 generates the charging power in the charge mode and does not generate the charging power in the standby mode.

Accordingly, when the user inputs the X-ray radiation ready command, the supply of the charging power may be stopped as illustrated on the right side of FIG. 5B. In addition, since the X-ray radiation command is not input yet, the operating power is not supplied.

Even when the X-ray source 111 is not actually operated, when the X-ray radiation ready command is input, the X-ray radiation command is highly likely to be input. Therefore, in order to prepare for the input of the X-ray radiation command, the controller 112 switches the charger 120 to the standby mode in advance and prevents overload of the charger 120.

Figure 5C:
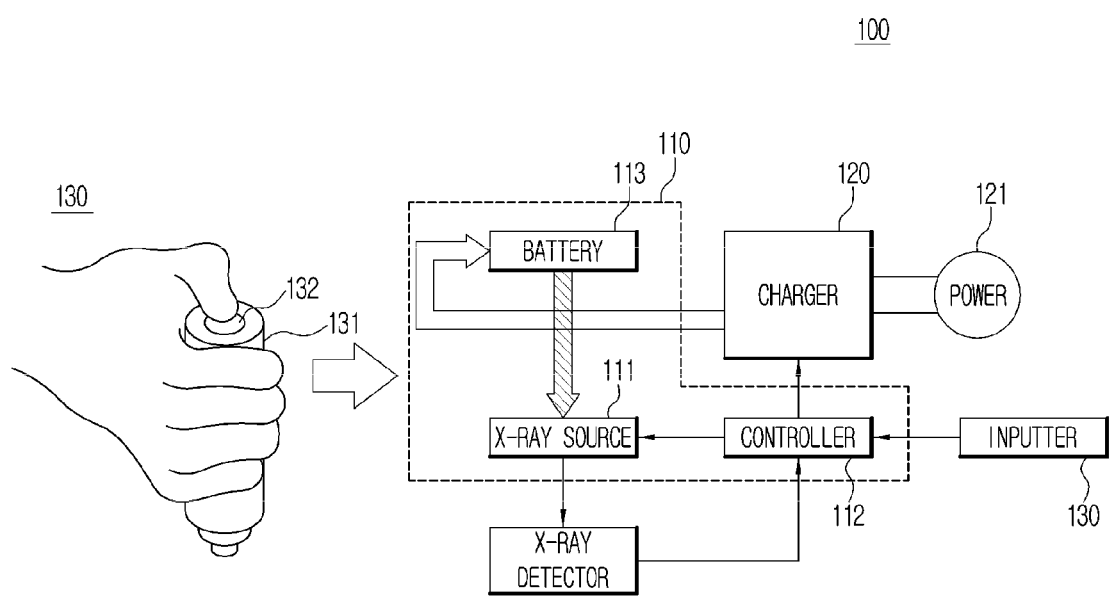

FIG. 5C exemplifies a case in which the X-ray radiation command is input to the mobile X-ray imaging apparatus while the battery is being charged.

As illustrated on the left side of FIG. 5C, the user may input the second command through the inputter 130. As described above, it is necessary to input the first command first in order to input the second command. Therefore, it is possible to input the X-ray radiation command in a state of FIG. 5B.

In order to supply power necessary for X-ray radiation, the battery 113 may generate the operating power. This generated operating power may be delivered from the battery 113 to the X-ray source 111 as illustrated in FIG. 5C. In this case, the path by which the operating power flows may be the operating power supplying path.

As illustrated on the right side of FIG. 5C, since the charger 120 is in the standby mode, the charging power is not generated. When the charging power enters the X-ray source 111, this could result in is an overload problem with the charger 120. However, since the charger 120 does not generate the charging power, this problem may not occur.

Figure 5D:
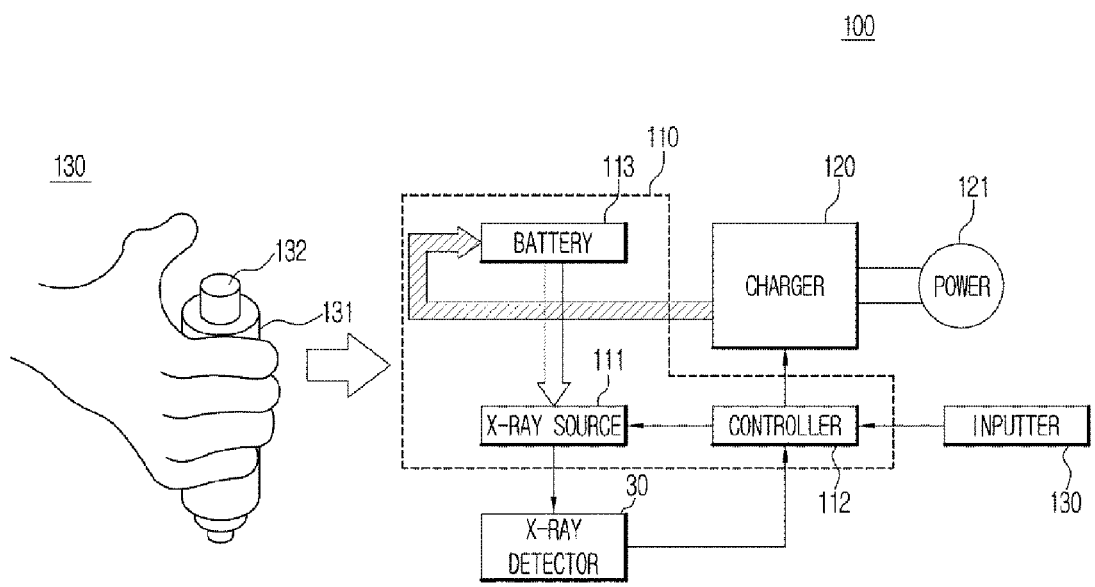

FIG. 5D exemplifies a case in which the battery is recharged again after the X-ray source radiates X-rays.

As illustrated on the left side of FIG. 5D, when the user determines that X-ray imaging has ended, the user may stopping pressing the button 132 of the inputter 130. That is the user can release the pressure being placed on the button 132. This means that there is no longer an input of the X-ray radiation ready command or the X-ray radiation command.

When the X-ray radiation ready command and the X-ray radiation command are not input, there is no need to supply power to the X-ray source 111. Therefore, even when the charging power is supplied in order to charge the battery 113, there is no risk of overloading the charger 120.

Therefore, as illustrated on the right side of FIG. 5D, when the X-ray radiation ready command and the X-ray radiation command are not input, the charger 120 supplies the charging power and charges the battery 113 again. In this case, as in FIG. 5A, the charging power may be delivered to the battery 113 along the charging power supplying path.

In viewing FIGS. 5A to 5D as a series of processes, when the user applies pressure to the button 132 of the inputter 130 and then releases the pressure, the charger 120 is switched from the charge mode to the standby mode and then switched to the charge mode again. Switching of the charger 120 to the standby mode is performed to prevent the charging power from entering the X-ray source 111 when X-rays are radiated. The charger 120 is switched to the standby mode in advance in an X-ray imaging ready operation, which is an operation performed before X-rays are radiated.

In this way, the X-ray radiation ready command is input and the charger 120 is switched to the standby mode. This is because the X-ray radiation command is highly likely to be input later. Therefore, there is no need to block the supply of the charging power when only the X-ray radiation ready command is input.

Accordingly, when the X-ray radiation command is not input within a predetermined time after the X-ray radiation ready command is input, the controller 112 may perform control such that the battery 113 is charged again. The predetermined time may be determined by a user of the X-ray imaging apparatus 100, or based on the operation being performed, however, these are merely examples.

Figure 6A:
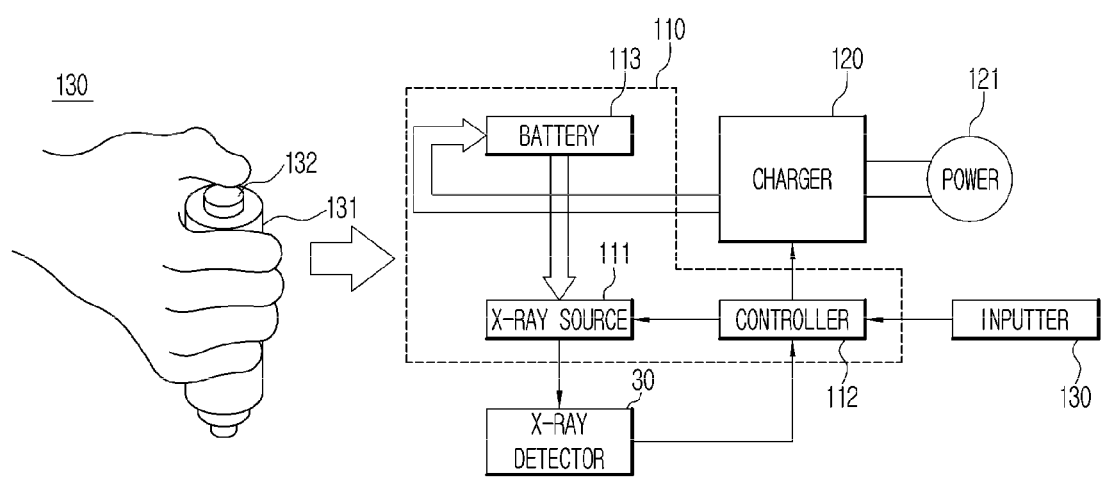
FIGS. 6A to 6C illustrate a series of control processes made by a user controlling a mobile X-ray imaging apparatus through an inputter according to another exemplary embodiment.
Figure 6B:
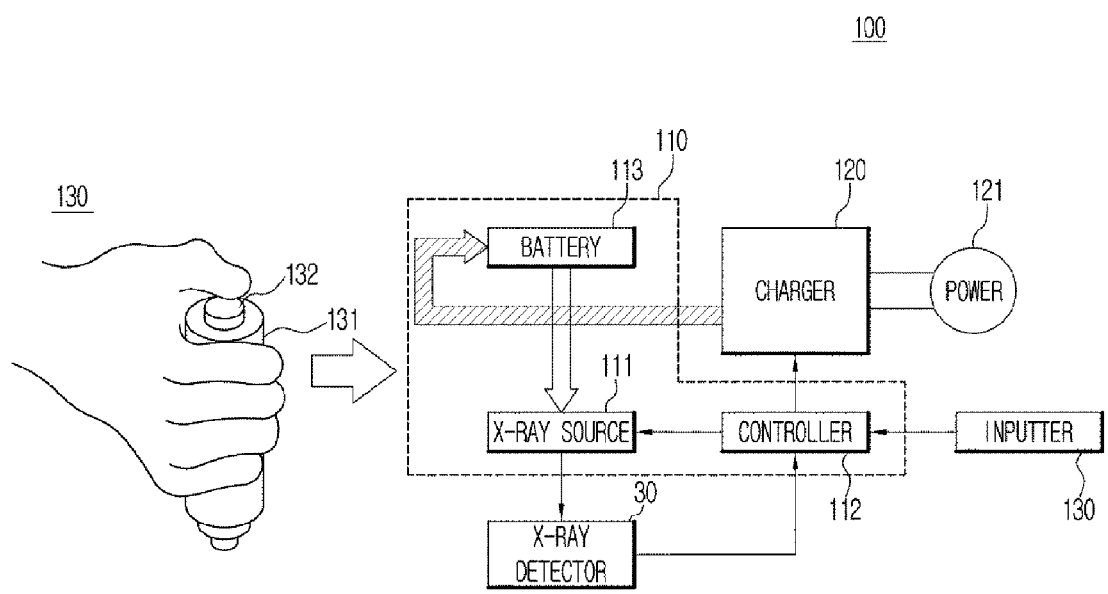
Figure 6C:
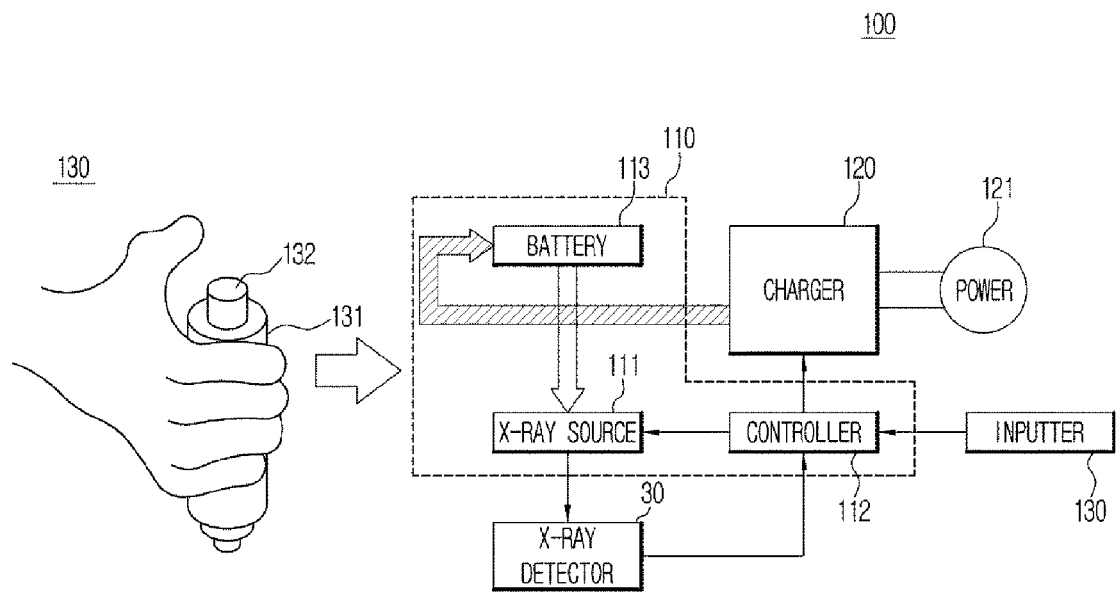

FIGS. 6A to 6C illustrate a series of control processes of the user controlling a mobile X-ray imaging apparatus through an inputter according to another exemplary embodiment. The left sides of FIGS. 6A to 6C illustrate a method of the user inputting a command through the inputter 130 according to another exemplary embodiment and the right sides of FIGS. 6A to 6C illustrate a method of controlling power supply according to the user's input according to another exemplary embodiment. A shaded section on the right side of FIGS. 6A to 6C indicates a power supply path. Hereinafter, it is assumed and described that FIGS. 6A to 6C are sequentially arranged according to an occurrence in time.

FIG. 6A exemplifies a case in which the X-ray radiation ready command is input to the mobile X-ray imaging apparatus while the battery is being charged.

As illustrated on the left in FIG. 6A, the user may input the first command to the charging mobile X-ray imaging apparatus 100 through the inputter 130. The first command may be the X-ray radiation ready command.

As illustrated on the right side of FIG. 6A, the controller 112 may switch the charger 120 to the standby mode in response to the X-ray radiation ready command. The charger 120 which has switched to the standby mode stops the generation of the charging power and thus the battery 113 is no longer being charged.

As described above, even when X-rays are not actually radiated, the charger 120 is switched to the standby mode. This is because when the X-ray radiation ready command is input, the X-ray radiation command is highly likely to be input next. Therefore, when the X-ray radiation command is not input, the controller 112 needs to control the charger 120 such that the battery 113 is charged again.

FIG. 6B exemplifies a case in which the X-ray radiation ready command is input to the charging mobile X-ray imaging apparatus and then the predetermined time has passed.

As illustrated on the left side of FIG. 6B, the user continuously applies pressure of a first threshold pressure or higher and less than a second threshold pressure to the button 132. In principle, since applying pressure of the first threshold pressure or higher and less than the second threshold pressure is the same as inputting of the X-ray radiation ready command, the controller 112 needs to block generation of the charging power by continuously switching the charger 120 to the standby mode. However, since the X-ray radiation command is not input within the predetermined time, the charger 120 is no longer maintained in the standby mode.

Here, the predetermined time may refer to a time by which the X-ray radiation command is usually input after the X-ray radiation ready command is input. This predetermined time may be input by the user through the inputter 130 or determined by operations in the apparatus.

As illustrated on the right side of FIG. 6B, since the X-ray radiation command is not input within the predetermined time after the X-ray radiation ready command is input, the controller 112 performs control such that the charger 120 is switched from the standby mode to the charge mode. As a result, the charger 120 generates the charging power and supplies the generated power to the battery 113. Therefore, it is possible to restart charging of the battery 113.

FIG. 6C exemplifies a case when the user releases the input from charging mobile X-ray imaging apparatus.

As illustrated on the left side of FIG. 6C, the user may release the X-ray radiation ready command rather than inputting the X-ray radiation command within the predetermined time after the X-ray radiation ready command is input.

At the time of releasing the X-ray radiation ready command, the controller 112 may perform control such that the charger 120 is switched from the standby mode to the charge mode. However, since the charger 120 is already switched to the charge mode and the battery 113 is being recharged in FIG. 6B, the mode of the charger 120 may not be switched even when the X-ray radiation ready command is released.

As illustrated on the right side of FIG. 6C, the controller 112 does not switch the mode of the charger 120 regardless of whether the user has released the X-ray radiation ready command. This is because the controller 112 has already performed control such that the charger 120 is switched from the standby mode to the charge mode in the operation of FIG. 6B. Therefore, the controller 112 may perform control such that the mode of the charger 120 is not switched, the current charge mode is maintained, and thus the charger 120 charges the battery 113.

Unlike the mobile X-ray imaging apparatus in FIG. 2, a switch 114 may also be used to prevent the charging power from entering the X-ray source 111.

Figure 7:
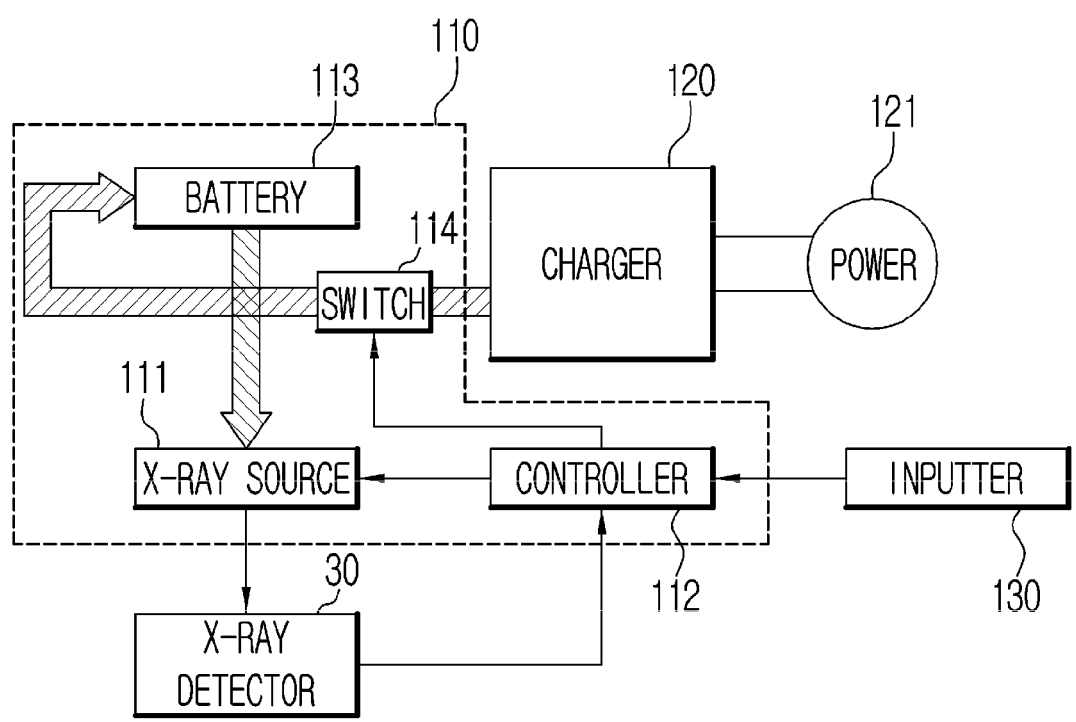
FIG. 7 is a control block diagram illustrating a mobile X-ray imaging apparatus according to another exemplary embodiment.

FIG. 7 is a control block diagram illustrating a mobile X-ray imaging apparatus according to another exemplary embodiment. In FIG. 7, a thin arrow indicates a flow of control and a thick arrow indicates a power supply path.

As illustrated in FIG. 7, the mobile X-ray imaging apparatus according to another exemplary embodiment may include the main body 110 having the X-ray source 111, the controller 112, and the battery 113, the X-ray detector 30, the inputter 130, and the charger 120, and may further include the switch 114.

Since a configuration further includes the switch 114 in addition to the configuration of the X-ray imaging apparatus of FIG. 2, a description of the same configuration elements will not be repeated. A description will be provided focusing on a method of the controller 112 controlling the switch 114.

The switch 114 may be provided in the charging power supplying path through which the charging power generated from the charger 120 is supplied to the battery 113. In particular, the switch 114 may be provided between a node closest to the charger 120 and the battery 113 in the charging power supplying path. However, this is only an example, and it is sufficient that the switch 114 be provided such that the charging power does not enter the X-ray source 111.

In addition, FIG. 7 exemplifies a case in which the switch 114 is provided inside the main body 110. However, the switch 114 may be provided outside of the main body 110 or inside the charger 120. When the switch 114 is provided in the charging power supplying path, a location thereof is not limited thereto. Hereinafter, it is assumed and described that the switch 114 is provided inside the main body 110.

The charging power supplying path may be connected in an on state of the switch 114 and the charging power supplying path may be disconnected in an off state thereof. In order to disconnect the charging power supplying path in an off state, the switch 114 may block a flow of power by disconnecting a physical connection or through electrical control. However, this is only an example. It is sufficient that the charging power is not delivered to the battery 113 and the X-ray source 111 through the charging power supplying path in an off state of the switch 114.

The controller 112 may turn on the switch 114 at the time of charging so that the charging power supplying path is connected and turn off the switch 114 at the time of radiating X-rays so that the charging power supplying path is disconnected. Hereinafter, a method in which the switch 114 is used to control such that the charging power does not enter the X-ray source 111 will be described with reference to FIGS. 8A and 8B.

Figure 8A:
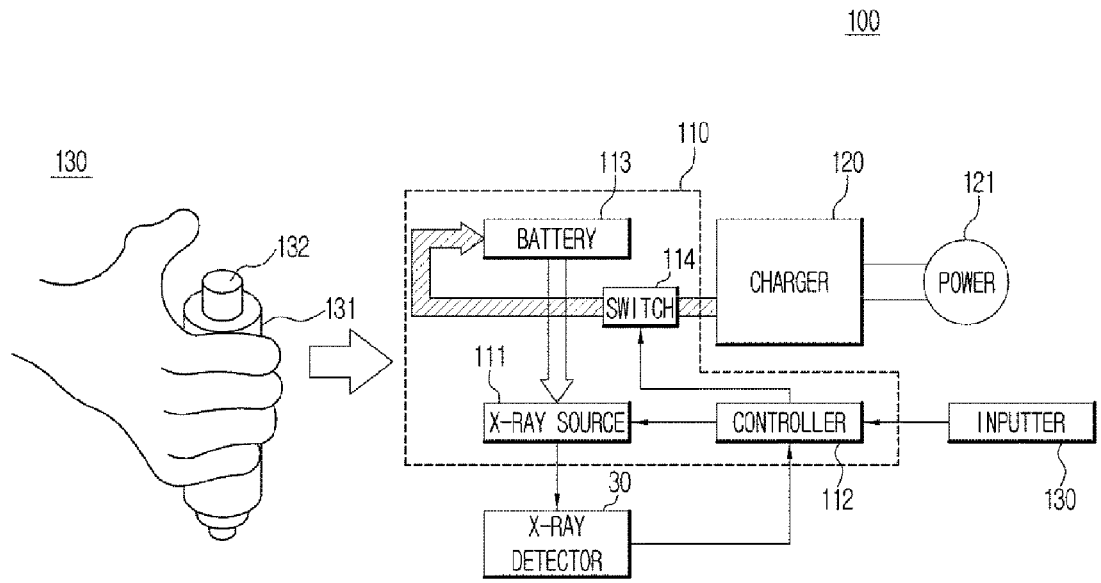
FIGS. 8A to 8D illustrate a series of control processes made by a user controlling a mobile X-ray imaging apparatus having a switch through an inputter according to an exemplary embodiment.
Figure 8B:
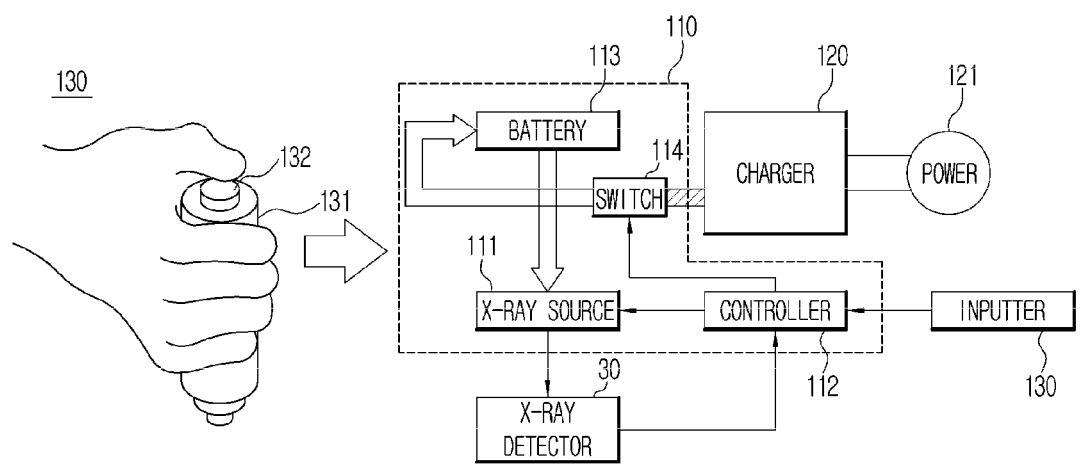

FIGS. 8A and 8B illustrate a series of control processes of a user controlling a mobile X-ray imaging apparatus having a switch through an inputter according to an exemplary embodiment. The left sides of FIGS. 8A to 8D illustrate a method of the user inputting a command through the inputter 130 according to the exemplary embodiment and the right sides of FIGS. 8A to 8D illustrate a method of controlling power supply by the user's input according to the exemplary embodiment. A shaded section on the right side of FIGS. 8A to 8D indicates a power supply path. Hereinafter, it is assumed and described that FIGS. 8A to 8D are sequentially arranged according to an occurrence in time.

FIG. 8A exemplifies a case in which the battery is being charged while no command is input to the mobile X-ray imaging apparatus. Since the battery 113 is being charged, the charger 120 may be set to the charge mode.

As illustrated on the left side of FIG. 8A, the user does not press the button 132 of the inputter 130. Not pressing the button 132 may include applying pressure of less than a first threshold pressure.

The controller 112 may turn on the switch 114 so that the charging power generated from the charger 120 is delivered to the battery 113. Specifically, the controller 112 turns on the switch 114 and thus the charging power supplying path is connected. Here, the charging power supplying path refers to a path through which the charging power is supplied and indicates a shaded section on the right side of FIG. 8A.

The charging power generated from the charger 120 may be delivered to the battery 113 along the charging power supplying path connected through the switch 114. Since the charger 120 is in a state in which the charging power can be generated, the charger 120 may be in the charge mode.

FIG. 8B exemplifies a case in which the X-ray radiation ready command is input to the mobile X-ray imaging apparatus while the battery is being charged.

When X-ray imaging is performed without control of the charging current, the charger 120 may be overloaded. Therefore, it is necessary to prevent the charging current from being delivered according to the user's predetermined input before X-rays are radiated.

As illustrated on the left side of FIG. 8B, the user may input the X-ray radiation ready command through the inputter 130. To this end, the user may apply pressure of the first threshold pressure or higher and less than a second threshold pressure to the button 132 of the inputter 130.

According to the user's input, the controller 112 may turn off the switch 114. As a result, as illustrated on the right in FIG. 8B, the charging power supplying path is disconnected and thus charging of the battery 113 may be stopped. In addition, since the X-ray radiation command is not yet input, the operating power is not supplied either.

On the other hand, unlike FIGS. 2 and 5A to 5D, when the switch 114 is used to prevent overload of the charger 120, there is no need to control the mode of the charger 120. As illustrated in FIG. 8B, since the charger 120 is in the charge mode, even when the charging power is generated, it is possible to disconnect the charging power supplying path using the switch 114.

Even when the X-ray source 111 does not actually operate, since X-rays are highly likely to be radiated later, when the X-ray radiation ready command is input, the switch 114 is turned off. The objective of this procedure is the same as in FIG. 5B.

Figure 8C:
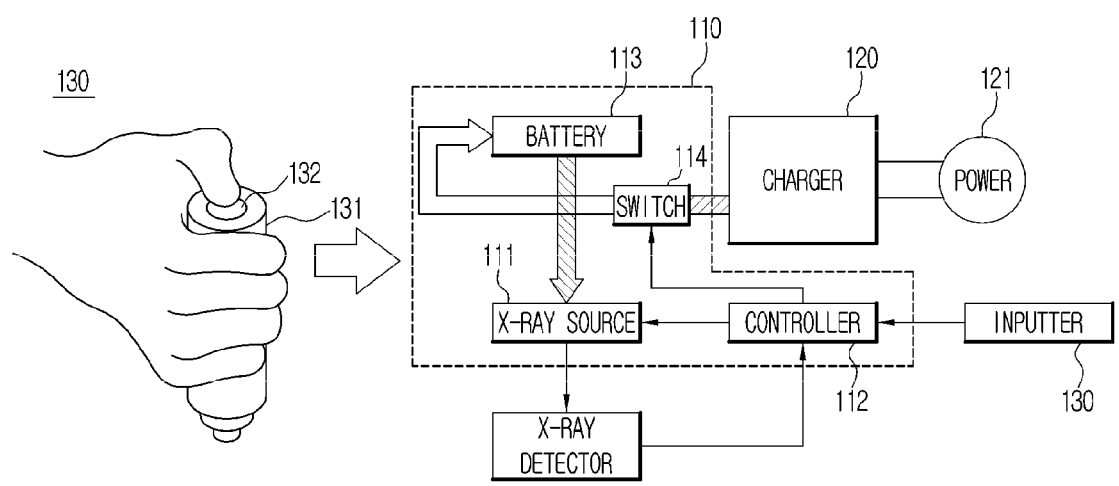

FIG. 8C exemplifies a case in which the X-ray radiation command is input to the mobile X-ray imaging apparatus while the battery is being charged.

As illustrated on the left side of FIG. 8C, the user may input the X-ray radiation command through the inputter 130. As described above, since it is necessary to input the X-ray radiation ready command in advance in order to input the X-ray radiation command, it is possible to input the X-ray radiation command in the state of FIG. 8B.

As illustrated in the right side of FIG. 8C, since the charger 120 is in the charge mode, it is possible to continuously generate the charging power. However, since the switch 114 is in an off state, the charging power supplying path is disconnected and thus the charging current no longer flows.

Alternatively, the battery 113 may supply the operating power to operate the X-ray source 111. On the right side of FIG. 8C, the operating power flows along the shaded section and is supplied to the X-ray source 111. This path may be the operating power supplying path.

When the charging power generated from the charger 120 is supplied to the X-ray source 111, overload of the charger 120 occurs. Therefore, it is possible to prevent this problem in advance by disconnecting the charging power supplying path using the switch 114.

Figure 8D:
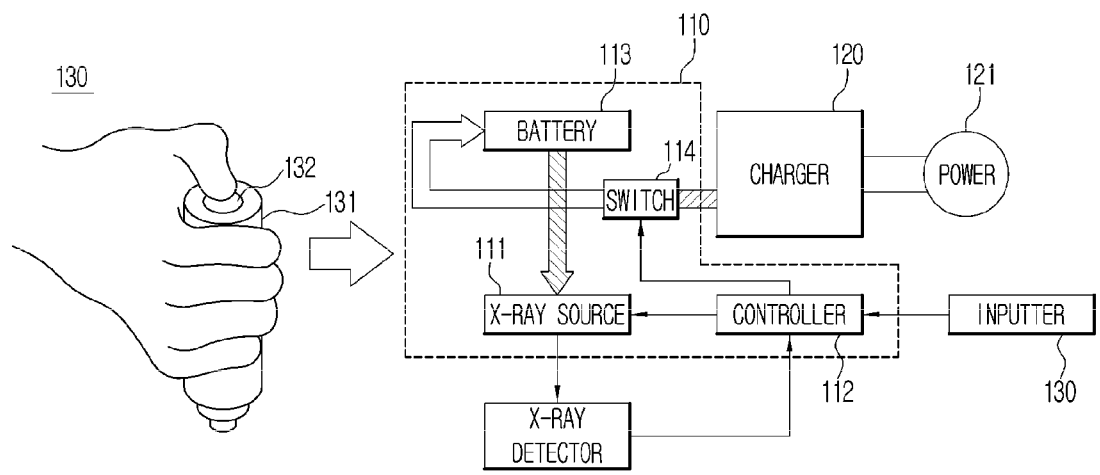

FIG. 8D exemplifies a case in which the battery is recharged again after the X-ray source radiates X-rays.

As illustrated on the left side of FIG. 8D, when the user determines that X-ray imaging has ended, the user may no longer input the X-ray radiation ready command and the X-ray radiation command to the button 132 of the inputter 130.

When the X-ray radiation ready command and the X-ray radiation command are not input, as illustrated on the right side of FIG. 8D, the charger 120 supplies the charging power and charges the battery 113 again. In this case, as in FIG. 8A, the charging power may be delivered to the battery 113 along the charging power supplying path.

In viewing FIGS. 8A to 8D as a series of processes, when the user applies pressure to the button 132 of the inputter 130 and then releases the pressure, the switch 114 is switched from an on state to an off state, and then switched to an on state again. When the switch 114 is turned off, the charging power supplying path is disconnected and thus it is possible to prevent the charging power from entering the X-ray source 111. That is, the switch 114 is turned off only when the X-ray source 111 radiates X-rays, and thus the charging power is prevented from entering the X-ray source 111.

Further, unlike FIGS. 5A to 5D, when the switch 114 is used, there is no need to control the mode of the charger 120. In order to control the mode of the charger 120, additional IO pins may be installed and a control signal for controlling the pins may be transmitted and received. However, when the switch 114 is installed, there is no need to install an additional configuration for transmitting and receiving a signal to and from the charger 120. It is sufficient if the switch 114 is installed in the charging power supplying path and the controller 112 is able to turn the switch 114 on or off.

Even when the charging power is prevented from entering the X-ray source 111 using the switch 114, the controller 112 may perform control such that the battery 113 starts charging again when the X-ray radiation command is not input within the predetermined time after the X-ray radiation ready command is input.

Figure 9A:
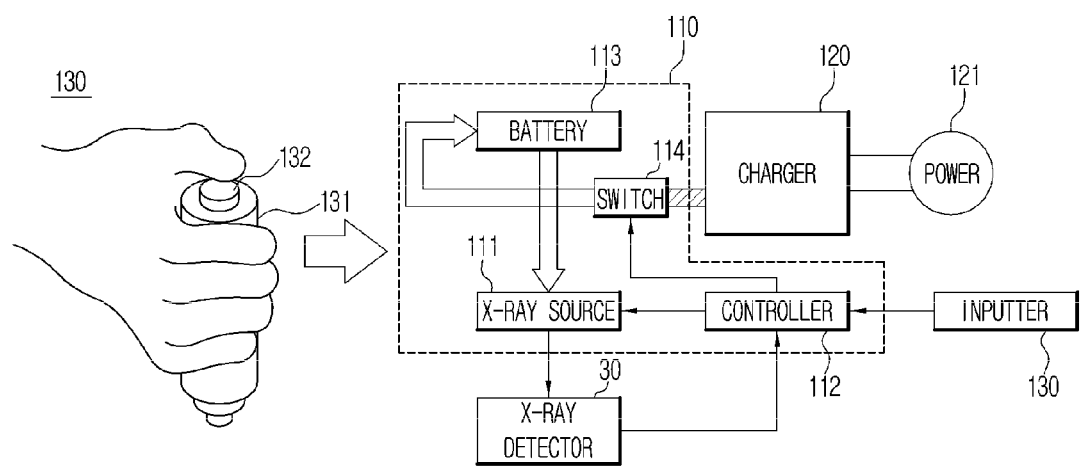
FIGS. 9A to 9C illustrate a series of control processes made by a user controlling a mobile X-ray imaging apparatus having a switch through an inputter according to another exemplary embodiment.
Figure 9B:
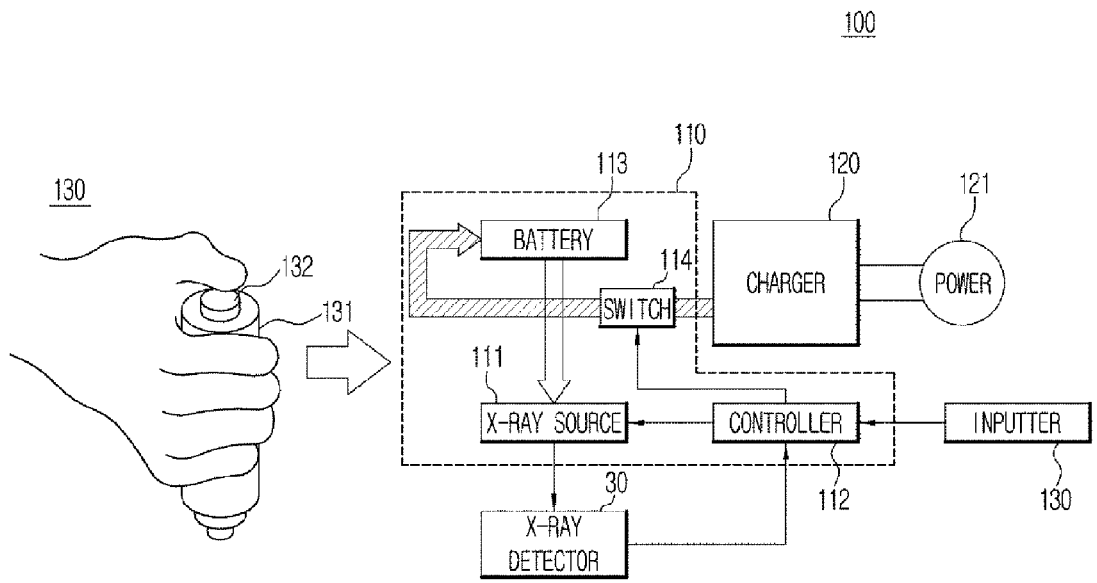
Figure 9C:
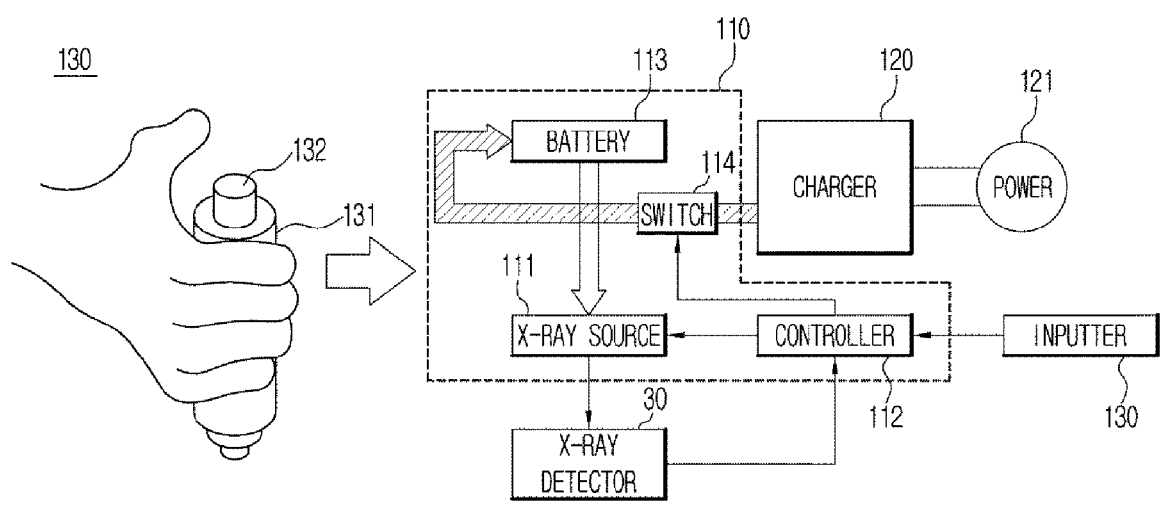

FIGS. 9A to 9C illustrate a series of control processes made by a user controlling a mobile X-ray imaging apparatus having a switch through an inputter according to another exemplary embodiment. The left sides of FIGS. 9A to 9C illustrate a method of the user inputting a command through the inputter 130 according to another exemplary embodiment and the right sides of FIGS. 9A to 9C illustrate a method of controlling power supply by the user's input according to another exemplary embodiment. A shaded section on the right side of FIGS. 9A to 9C indicates a power supply path. Hereinafter, it is assumed and described that FIGS. 9A to 9C are sequentially arranged according to an occurrence in time.

FIG. 9A exemplifies a case in which the X-ray radiation ready command is input to the mobile X-ray imaging apparatus while the battery is being charged.

As illustrated on the left side of FIG. 9A, the user may input the X-ray radiation ready command to the charging mobile X-ray imaging apparatus through the inputter 130.

As illustrated on the right side of FIG. 9A, the controller 112 may turn off the switch 114 in response to the X-ray radiation ready command of the user. When the switch 114 is turned off, the charging power supplying path may be disconnected. As a result, it is possible to prevent the charging power from flowing along the charging power supplying path.

However, even when the switch 114 is used to control the charging power, it is necessary to perform control such that the battery 113 starts charging again when the X-ray radiation command is not input within the predetermined time after the X-ray radiation ready command is input.

FIG. 9B exemplifies a case in which the X-ray radiation ready command is input to the charging mobile X-ray imaging apparatus and then the predetermined time passes.

As illustrated on the left in FIG. 9B, the user may continuously input the X-ray radiation ready command. In principle, the controller 112 needs to turn off the switch 114 in response to the user's input. However, since the X-ray radiation command is not input within the predetermined time, there is no further need to block supply of the charging power.

Here, the predetermined time may refer to a time by which the X-ray radiation command is usually input after the X-ray radiation ready command is input. This predetermined time may be input by the user through the inputter 130 or determined by operations in the apparatus.

As illustrated on the right side of FIG. 9B, since the X-ray radiation command is not input within the predetermined time after the X-ray radiation ready command is input, the controller 112 may turn on the switch 114 so that the charging power supplying path is connected again. As a result, the charging power generated from the charger 120 is supplied to the battery 113 along the charging power supplying path and thus it is possible to start charging of the battery 113 again.

FIG. 9C exemplifies a case when the user releases the input from the charging mobile X-ray imaging apparatus.

As illustrated on the left side of FIG. 9C, the user may release the X-ray radiation ready command rather than inputting the X-ray radiation command within the predetermined time after the X-ray radiation ready command is input.

At the time of releasing the X-ray radiation ready command, the controller 112 may switch the switch 114 from an off state to an on state. However, since the switch 114 is already switched to the on state in FIG. 9B, even when the X-ray radiation ready command is released, the state of the switch 114 may not be switched.

As illustrated on the right side of FIG. 9C, regardless of whether the user has released the X-ray radiation ready command, the controller 112 may maintain the switch 114 in the on state so that the charging power supplying path is not disconnected. As a result, the charging power generated from the charger 120 is stably supplied to the battery 113 and thus the battery may be charged.

FIG. 10 is a flowchart illustrating a method of controlling a mobile X-ray imaging apparatus according to an exemplary embodiment. In the flowchart of FIG. 10, a control method that is applied to the mobile X-ray imaging apparatus described in FIG. 2 is used, however, the exemplary embodiment is not limited to this example.

First, charging of the battery starts (S300). Specifically, the user may switch the charger 120 to the charge mode. Since the charger 120 generates the charging power in the charge mode, the battery 113 may be charged when the charging power is supplied from the charger 120 to the battery 113.

While the battery is being charged, the user may input the X-ray radiation ready command (S310). When the X-ray radiation ready command is input, since X-rays are highly likely to be radiated later, it is necessary to take measures so as to prevent overloading the charger 120.

In order to prevent the charger 120 from being overloaded, it is possible to switch the charger to the standby mode (S320). When the charger 120 continuously generates the charging power, the charging power may enter the X-ray source 111 at the time of radiating X-rays later. As a result, the charger 120 may be overloaded. Therefore, the charger 120 is switched from the charge mode to the standby mode, and thus it is possible to stop generation of the charging power in an exemplary embodiment.

After the charger is switched to the standby mode, it is possible to determine whether the X-ray radiation command is input within a predetermined time t0 (S330). When the X-ray radiation ready command is input, the switch 114 is turned off. This is because it is assumed that the X-ray radiation command will be input later. Therefore, it is necessary to determine whether the X-ray radiation command is input after the X-ray radiation ready command is input.

When the X-ray radiation command is input within the predetermined time t0, the X-ray source 111 may radiate X-rays (S340). It is determined whether X-rays need to be further radiated. When it is determined that X-rays need to be further radiated, X-rays may be repeatedly radiated.

When it is determined that the X-ray radiation command is not input within the predetermined time t0 or X-rays are sufficiently radiated (S350), the charger may be switched to the charge mode again (S360). Since overload of the charger 120 occurs while X-rays are radiated, when X-ray radiation ends or the X-ray radiation command is not input, overload of X-rays does not occur even when the battery 113 is being charged.

When the charger is switched to the charge mode, the charger generates the charging power again and supplies the generated power to the battery. Therefore, it is possible to restart charging of the battery (S370). The charger 120 may supply the charging power until the battery 113 is completely charged. When the battery 113 is completely charged, the charger 120 is switched to the standby mode and thus supplying the charging power may be stopped.

FIG. 11 is a flowchart illustrating a method of controlling a mobile X-ray imaging apparatus according to another exemplary embodiment. In the flowchart of FIG. 11, a control method that is applied to the mobile X-ray imaging apparatus described in FIG. 7 is used, however, the exemplary embodiment is not limited to this example.

Similarly to FIG. 10, first, the battery starts charging (S400). Specifically, the charging power generated from the charger 120 is supplied to the battery 113 along the charging power supplying path and thus the battery 113 may be charged.

The user may input the X-ray radiation ready command while the battery is being charged (S410). After the X-ray radiation ready command is input, since X-ray radiation is expected, it is necessary to take measures so as to prevent overloading the charger 120.

In order to prevent overloading the charger, the switch may be turned off (S420). In this case, the switch 114 may be provided in the charging power supplying path. In particular, the switch 114 may be provided between a node closest to the charger 120 and the battery 113 in the charging power supplying path.

When the switch 114 is turned off, the charging power supplying path is disconnected. As a result, the charging power generated from the charger 120 may not flow along the charging power supplying path and charging of the battery 113 may be stopped.

After the switch is turned off, it is possible to determine whether the X-ray radiation command is input within the predetermined time t0 (S430). This is because there is no reason to stop charging of the battery 113 when the X-ray radiation command is not input after the X-ray radiation ready command is input.

When the X-ray radiation command is input within the predetermined time t0, the X-ray source may radiate X-rays (S440). It is determined whether X-rays need to be further radiated. When it is determined that X-rays need to be further radiated, X-rays may be repeatedly radiated.

When it is determined that the X-ray radiation command is not input within the predetermined time t0 or X-rays are sufficiently radiated (S450), the switch may be turned on again (S460). When X-ray radiation has ended or the X-ray radiation command is not input, overload of X-rays does not occur even when the battery 113 is being charged.

When the switch is turned on again and the charging power supplying path is connected, the charger generates the charging power again and supplies the generated power to the battery. Therefore, it is possible to restart charging of the battery (S470). The charger 120 may supply the charging power until the battery 113 is completely charged. When the battery 113 is completely charged, the charger 120 is switched to the standby mode and thus supply of the charging power may be stopped as in FIG. 10.

What is claimed is:

1. A mobile X-ray imaging apparatus comprising:
   an X-ray source mounted in a movable main body;
   a battery configured to supply operating power to the X-ray source;
   a charger configured to supply charging power to charge the battery; and
   a controller configured to block charging of the battery while X-rays are radiated.

2. The apparatus according to claim 1, wherein a supply path of the operating power and a supply path of the charging power form at least one node.

3. The apparatus according to claim 1, further comprising a switch provided in the supply path of the charging power.

4. The apparatus according to claim 3, wherein the controller is configured to turn off the switch and block charging of the battery.

5. The apparatus according to claim 1, wherein the controller is configured to switch the charger to a standby mode and block charging of the battery.

6. The apparatus according to claim 5, wherein the charger is configured to not generate the charging power in the standby mode.

7. The apparatus according to claim 1, further comprising an inputter configured to receive an X-ray radiation ready command and an X-ray radiation command,
   wherein the controller is configured to block charging of the battery when the X-ray radiation ready command is input.

8. The apparatus according to claim 7, wherein the controller is configured to perform control such that the charging of the battery is restarted when the radiation command is not input within a predetermined time after the ready command is input.

9. A method of controlling a mobile X-ray imaging apparatus which includes a movable main body, a battery configured to supply operating power to the main body, and a charger configured to supply charging power to charge the battery, the method comprising:
   determining whether X-rays are radiated when the charging power is supplied to the battery; and
   blocking supply of the charging power to the battery when it is determined that the X-rays are radiated.

10. The method according to claim 9, wherein, in the mobile X-ray imaging apparatus, a supply path of the operating power and a supply path of the charging power form at least one node.

11. The method according to claim 9, wherein the mobile X-ray imaging apparatus further includes a switch provided in the supply path of the charging power.

12. The method according to claim 11, wherein the blocking the supply of the charging power to the battery includes turning off the switch.

13. The method according to claim 9, wherein the blocking the supply of the charging power to the battery includes switching the charger to a standby mode.

14. The method according to claim 13, wherein the charger does not generate the charging power in the standby mode.

15. The method according to claim 9, wherein the determining whether the X-rays are radiated is performed by verifying whether an X-ray radiation ready command is input through an inputter.

16. The method according to claim 15, further comprising restarting charging of the battery when an X-ray radiation command is not input within a predetermined time after the ready command is input.

17. A mobile X-ray imaging apparatus comprising:
an X-ray source mounted in a movable main body;
a battery configured to supply operating power to the X-ray source;
a charger configured to supply charging power to charge the battery;
a controller configured to block charging of the battery while X-rays are radiated,
an inputter configured to receive a command,
a switch provided in a supply path of the charging power, wherein when the switch is turned on via the inputter, the supply path of the charging power is disconnected, and when the switch turned off via the inputter, the supply path of the charging power is connected.

* * * * *